United States Patent
Wang et al.

(10) Patent No.: US 12,125,175 B2
(45) Date of Patent: Oct. 22, 2024

(54) METHODS AND SYSTEM FOR SELECTIVE REMOVAL OF STREAK ARTIFACTS AND NOISE FROM IMAGES USING DEEP NEURAL NETWORKS

(71) Applicant: GE Precision Healthcare LLC, Wauwatosa, WI (US)

(72) Inventors: Xinzeng Wang, Carrollton, TX (US); Daniel Vance Litwiller, Denver, CO (US); Sagar Mandava, Atlanta, GA (US); Robert Marc Lebel, Calgary (CA); Graeme Colin Mckinnon, Hartland, WI (US); Ersin Bayram, Houston, TX (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 436 days.

(21) Appl. No.: 17/718,697

(22) Filed: Apr. 12, 2022

(65) Prior Publication Data
US 2022/0237748 A1  Jul. 28, 2022

Related U.S. Application Data

(62) Division of application No. 16/827,422, filed on Mar. 23, 2020, now Pat. No. 11,341,616.

(51) Int. Cl.
| | |
|---|---|
| *G06T 5/70* | (2024.01) |
| *G06N 3/08* | (2023.01) |
| *G06T 7/00* | (2017.01) |
| *G06V 10/82* | (2022.01) |
| *G16H 30/40* | (2018.01) |

(52) U.S. Cl.
CPC ............ *G06T 5/70* (2024.01); *G06N 3/08* (2013.01); *G06T 7/0012* (2013.01); *G06V 10/82* (2022.01); *G16H 30/40* (2018.01); *G06T 2207/10081* (2013.01); *G06T 2207/10088* (2013.01); *G06T 2207/20084* (2013.01); *G06T 2207/30004* (2013.01)

(58) Field of Classification Search
CPC . G06T 2207/20081; G06T 2207/20084; G06T 2211/441; G06V 10/82
See application file for complete search history.

(56) References Cited

U.S. PATENT DOCUMENTS 11,341,616 B2 *  5/2022  Wang ............... G16H 30/40
2018/0374245 A1 * 12/2018  Xu .................... A61B 6/563
(Continued)

FOREIGN PATENT DOCUMENTS

CN      110009613 A  *  7/2019
WO   WO-2020182710 A1 *  9/2020  .......... G06F 18/232

*Primary Examiner* — Gandhi Thirugnanam

(57) ABSTRACT

Methods and systems are provided for independently removing streak artifacts and noise from medical images, using trained deep neural networks. In one embodiment, streak artifacts and noise may be selectively and independently removed from a medical image by receiving the medical image comprising streak artifacts and noise, mapping the medical image to a streak residual and a noise residual using the trained deep neural network, subtracting the streak residual from the medical image to a first extent, and subtracting the noise residual from the medical image to a second extent, to produce a de-noised medical image, and displaying the de-noised medical image via a display device.

8 Claims, 11 Drawing Sheets

(56) References Cited

U.S. PATENT DOCUMENTS

| | | | |
|---|---|---|---|
| 2020/0196973 A1* | 6/2020 | Zhou | G06N 3/045 |
| 2021/0012543 A1* | 1/2021 | Hein | G06T 11/008 |
| 2021/0204884 A1* | 7/2021 | Ravishankar | A61B 5/316 |
| 2021/0295474 A1* | 9/2021 | Wang | G16H 30/40 |
| 2022/0199228 A1* | 6/2022 | Arteta | G16H 30/20 |
| 2022/0237748 A1* | 7/2022 | Wang | G06T 5/60 |
| 2023/0029188 A1* | 1/2023 | Langoju | G06T 7/0012 |

* cited by examiner

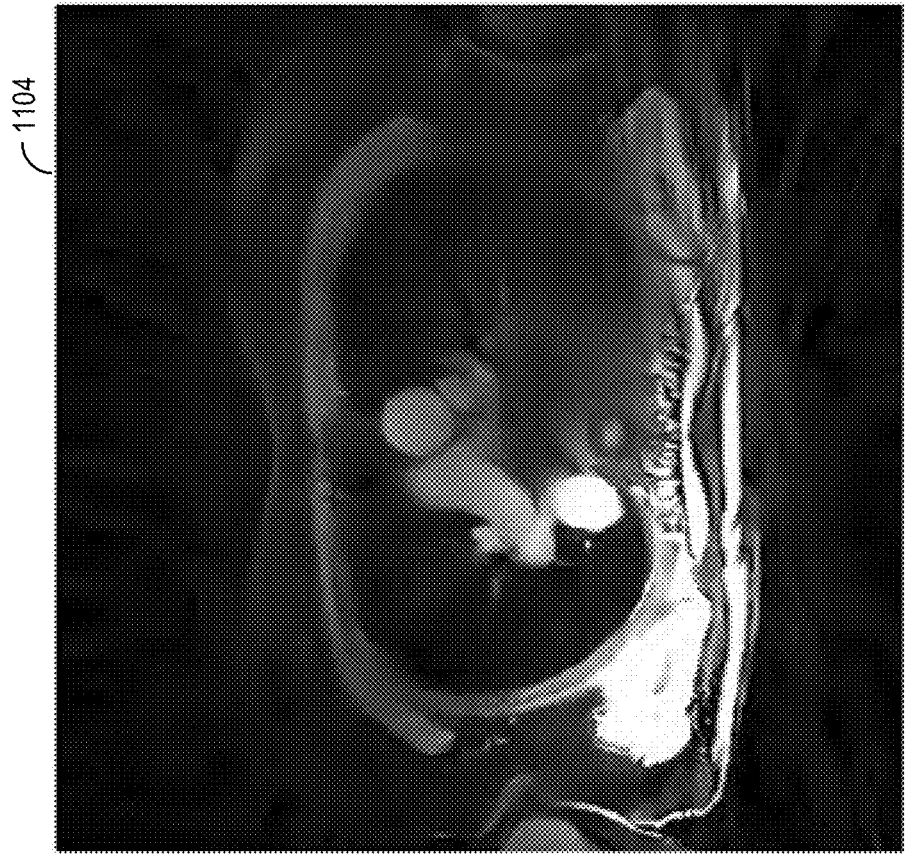
FIG. 11

METHODS AND SYSTEM FOR SELECTIVE REMOVAL OF STREAK ARTIFACTS AND NOISE FROM IMAGES USING DEEP NEURAL NETWORKS

CROSS REFERENCE TO RELATED APPLICATIONS

This Application is a divisional of U.S. patent application Ser. No. 16/827,422, filed Mar. 23, 2020, which application is herein incorporated by reference in its entirety.

TECHNICAL FIELD

Embodiments of the subject matter disclosed herein relate to magnetic resonance imaging (MRI) and computed tomography (CT) imaging, and more particularly, to systems and methods for removing streak artifacts and noise from MRI and CT images using deep neural networks.

BACKGROUND

Medical imaging systems are often used to obtain internal physiological information of a subject, such as a patient. For example, a medical imaging system may be used to obtain images of the bone structure, the brain, the heart, the lungs, and various other features of a patient. Medical imaging systems may include magnetic resonance imaging (MRI) systems, computed tomography (CT) systems, x-ray systems, ultrasound systems, and various other imaging modalities.

One drawback associated with MRI systems, and CT systems, is the time intensive nature of acquiring measurement data of an anatomical region of a patient, and reconstructing a medical image of the anatomical region from the measurement data. Slow image acquisition and reconstruction speed may lead to patient discomfort, as the patient may need to remain within an imaging system for an unpleasantly long duration of time as complete measurement data is acquired. Further, slow image acquisition and reconstruction may be incompatible with some imaging applications, such as in as in real-time imaging, where image acquisition and reconstruction latency may lead to poor temporal resolution.

One approach directed to increasing image acquisition and reconstruction speed employs incomplete acquisition/sampling of measurement data (e.g., undersampled k-space sampling in MRI, or incomplete acquisition of x-ray projection data in CT). Although incomplete acquisition of measurement data may increase image acquisition speed, images reconstructed from incomplete measurement data may include imaging artifacts, such as streak artifacts, and may further display a reduced signal-to-noise ratio (SNR). In addition to increasing acquisition speed, some medical images may be reconstructed from incomplete measurement data if part of the measurement data is rejected or reweighted due to the presence of motion.

One approach to reduce or remove the imaging artifacts in medical images reconstructed from incomplete measurement data utilizes sophisticated reconstruction techniques to produce artifact-free images. One example of such an approach is compressed sensing (CS). However, CS reconstruction is computationally intensive, and the optimization of reconstruction parameters is time-consuming Thus, CS may reduce imaging artifacts in medical images reconstructed from incomplete measurement data, at the expense of a longer and more complicated reconstruction process. In many cases, the increase in image reconstruction time introduced by CS may nullify the time gained by incomplete sampling of measurement data. Therefore, it is generally desirable to explore new approaches for more rapidly removing imaging artifacts from medical images reconstructed using incomplete measurement data.

SUMMARY

The inventors herein have identified systems and methods for selectively and independently removing streak artifacts and noise from medical images using deep neural networks, in a more rapid and computationally efficient manner than conventional approaches. In one embodiment, streak artifacts and noise may be removed from medical images by a method comprising, receiving a medical image comprising streak artifacts and noise, mapping the medical image to a streak residual and a noise residual using the trained deep neural network, subtracting the streak residual from the medical image to a first extent, and subtracting the noise residual from the medical image to a second extent, to produce a de-noised medical image, and displaying the de-noised medical image via a display device. By mapping the medical image to a streak residual and a noise residual, as opposed to mapping the medical image directly to a de-noised medical image, the extent of streak removal and the extent of noise removal may be selected independently of each other, providing greater flexibility and control over the appearance of the de-noised medical image.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which:

FIG. 11 shows a medical image comprising streak artifacts and noise, and a de-noised medical image produced according to an exemplary embodiment of the current disclosure.

Figure 1:
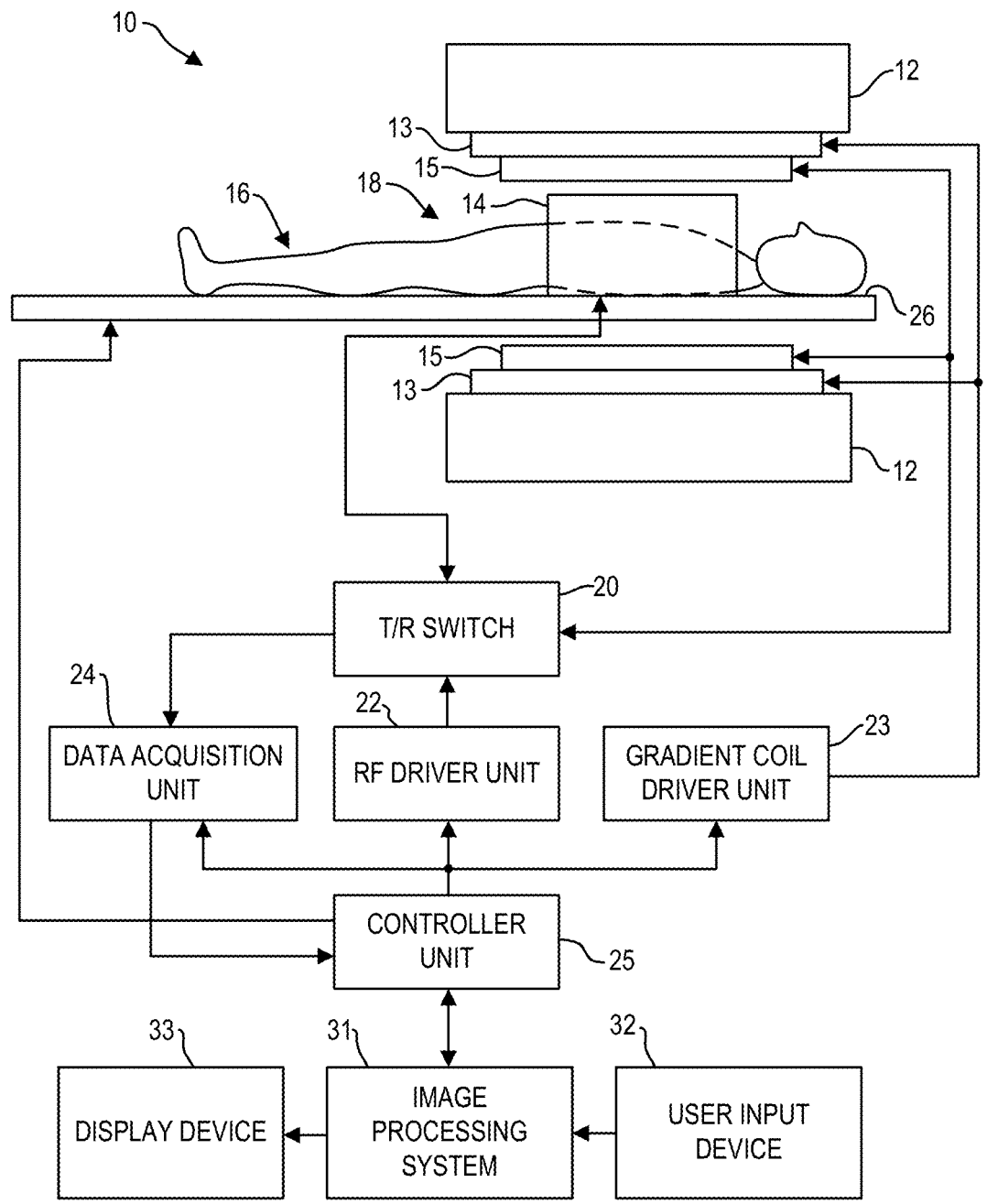
FIG. 1 shows a block diagram of an exemplary embodiment of an MRI system.

The drawings illustrate specific aspects of the described systems and methods for selectively removing streak artifacts and noise from MRI and CT images, using deep neural networks. Together with the following description, the drawings demonstrate and explain the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

The following description relates to systems and methods for automatically and selectively removing streak artifacts and noise from images. Certain magnetic resonance imaging (MRI) sequences, and computed-tomography (CT) imaging protocols, may be prone to noise and streak artifacts, which limits image resolution and degrades diagnostic quality. One source of streak artifacts is under-sampling in k-space, which may result from non-Cartesian sampling patterns (e.g., radial sampling patterns, spiral sampling patterns, etc.) used to enable shorter scan time, or to mitigate the impact of motion induced blur. In another example, k-space may also be under-sampled if part of the measurement data is rejected or reweighted due to the presence of motion. In one example, in Periodically Rotated Overlapping ParallEL Lines with Enhanced Reconstruction (PROPELLER) imaging, if there is substantial motion induced blurring in an acquired blade of k-space, the blade may be rejected to reduce the motion artifact, resulting in under-sampled k-space. In another example, for low dose CT imaging, sparse views or limited angles are acquired to reduce radiation exposure of an imaging subject, but CT images reconstructed from sparse or limited angles may be degraded by noise and streak artifacts. Fast scan and/or under-sampled k-space can also result in reduced Signal-to-Noise Ratio (SNR) and low image quality. Conventional approaches used to mitigate streak artifacts and noise in images produced from under-sampled measurement data (e.g., k-space, or sinogram data) employ sophisticated reconstruction techniques to produce artifact-free images from incomplete measurement data. One example is compressed sensing (CS). However, CS reconstruction is computationally intensive, and the optimization of reconstruction parameters is challenging.

Further, conventional approaches do not provide the ability to separately/independently control an extent of streak artifact removal and an extent of noise removal, giving a user little control over the appearance of a de-noised medical image. In one example, a conventional approach may include training a deep neural network using pairs of noisy medical images (e.g., medical images comprising both streak artifacts and noise), and corresponding pristine medical images (e.g., the same medical images without streak artifacts and noise). The deep neural networks trained according to conventional methods may therefore learn a mapping from a noisy image space to a pristine/de-noised image space. Deep neural networks produced according to conventional image de-noising training schemes, such as the one described above, do not enable a user to independently control an extent of removal of distinct types of artifacts, nor do they allow for variable removal of image artifacts. Thus, de-noised medical images produced according to conventional approaches provide a user with little or no ability to customize/adjust the extent of removal of the one or more types of noise present in the de-noised medical image. In one example, in instances where the deep neural network mis-identifies portions of an imaged anatomical region as noise/artifact, and therefore removes/alters said portions, a user may be unable to tune the extent of removal/alteration of said portion.

The current disclosure provides systems and methods which at least partially address one or more of the above identified issues. In one embodiment, an MRI image of an anatomical region of a patient, acquired by MRI system 10 of FIG. 1, may be transmitted to image processing device 202, shown in FIG. 2. The MRI image may include streak artifacts and noise. In some embodiments, the MRI system 10 may acquire the MRI image using a radial k-space undersampling pattern, wherein k-space is under-sampled in order to reduce a duration of image acquisition. In some embodiments, the MRI system 10 may include the image processing device 202, or image processing device 202 may be located external to the MRI system and may be communicably coupled to the MRI system 10. The image processing device 202 may include non-transitory memory 206 including a trained deep neural network, such as deep neural network 324 shown in FIG. 3. Deep neural network 324 may be configured to map received streaky-noisy medical images, such as streaky-noisy image 304, to streak residuals and noise residuals, such as streak residual 306 and noise residual 308, respectively. In some embodiments, deep neural network 324 may further be configured to receive one or more acquisition parameters, such as a k-space sampling pattern used to acquire the streaky-noisy medical image 304, as input at an input layer of the deep neural network 324, thereby providing deep neural network 324 with additional contextual information regarding the streaky-noisy medical image 304.

Figure 4:
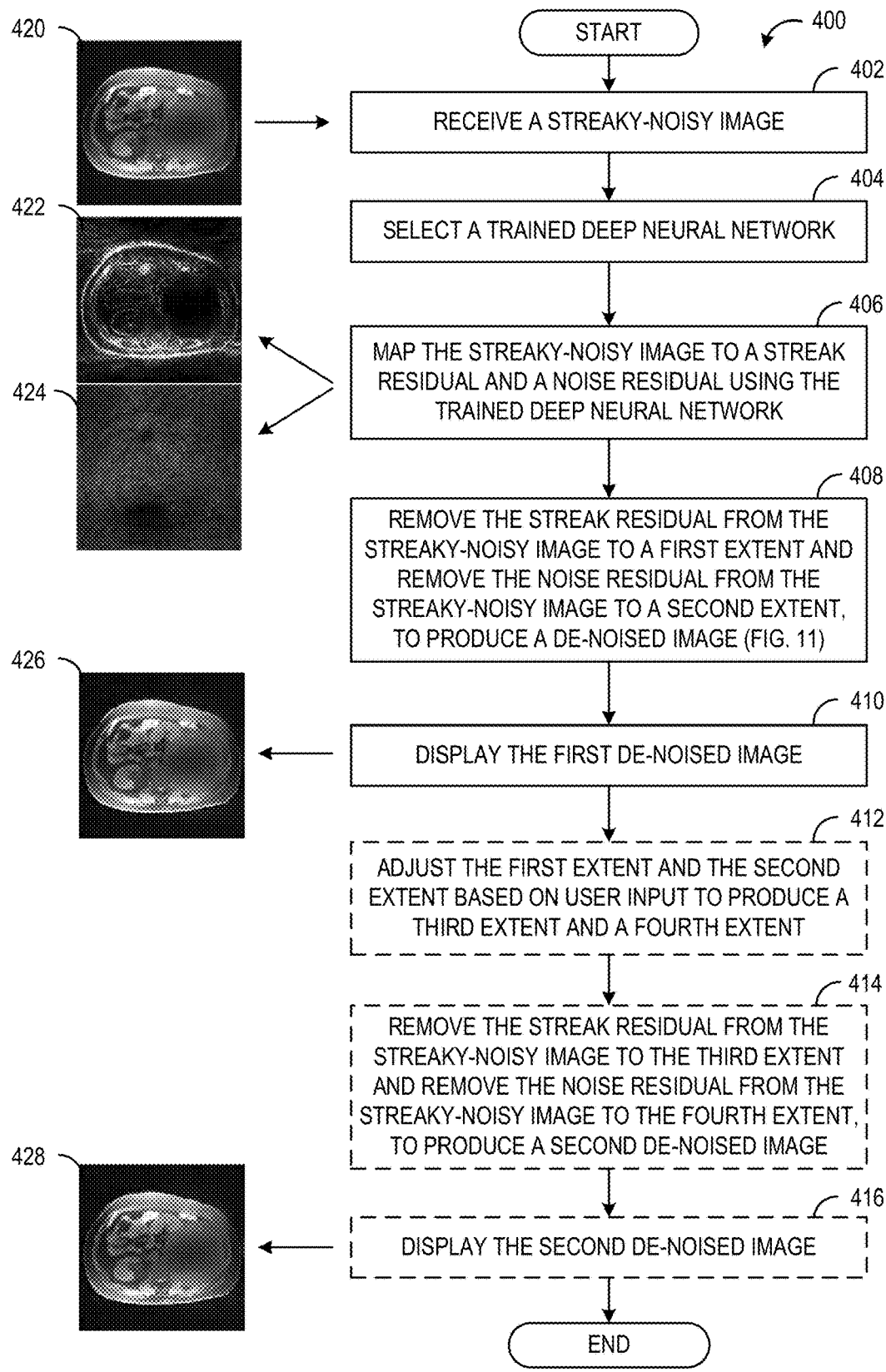
FIG. 4 is a flow chart illustrating an exemplary method for selectively removing streak artifacts and noise from a medical image using a trained deep neural network.

The image processing device 202 may further include instructions stored in non-transitory memory 206, that when executed, causes processor 204 to implement one or more of the operations of method 400, shown in FIG. 4, to selectively remove the streak residual and/or the noise residual output by the deep neural network from the MRI image based on a first weight and a second weight, respectively. Further, the image processing device 202 may comprise instructions for further adjusting an extent of removal of the streak residuals and an extent of the noise residuals based on user input received via a user input device. FIG. 11 shows a comparison between streaky-noisy medical image 1102, and a de-noised medical image 1104, wherein the de-noised medical image 1104 was produced by mapping the streaky-noisy medical image 1102 to a streak residual and a noise residual, and selectively subtracting the streak residual and the noise residual from the streaky-noisy image according to one or more of the operations of method 400, to produce the de-noised medical image 1104.

The current disclosure further provides systems and methods for training deep neural networks to map streaky-noisy images to streak residuals and noise residuals, wherein deep neural networks so trained may be employed in one or more of the methods described herein for removing streak artifacts and noise. Training data triads for training the deep neural network may be generated by executing one or more of the operations of method 500, shown in FIG. 5. In one example, the imaging processing device 202 may execute one or more of the operations of method 500 to generate a plurality of training data triads, wherein the plurality of training data triads may be used in conjunction with a training method, such as method 600, to teach a deep neural network a mapping from an image space to a streak residual space and a noise space. In one embodiment the trained deep neural network may comprise a plurality of parameters, enabling the trained deep neural network to identify and extract streak residuals and noise residuals from imaging data. The parameters may be learned by execution of one or more supervised training routines, such as training method 600 (shown in FIG. 6). Training method 600 comprises feeding the deep neural network training data triads, comprising streaky-noisy images and corresponding ground-truth streak residuals and ground-truth noise residuals, as input data, predicting a streak residual and a noise residual based on the input data, and comparing the predicted streak residual and the predicted noise residual against a ground-truth streak residual and a ground-truth noise residual. The parameters of the deep neural network may then be adjusted/updated based on the comparison to bring the deep neural network predictions closer to the ground-truth output.

Figure 7:
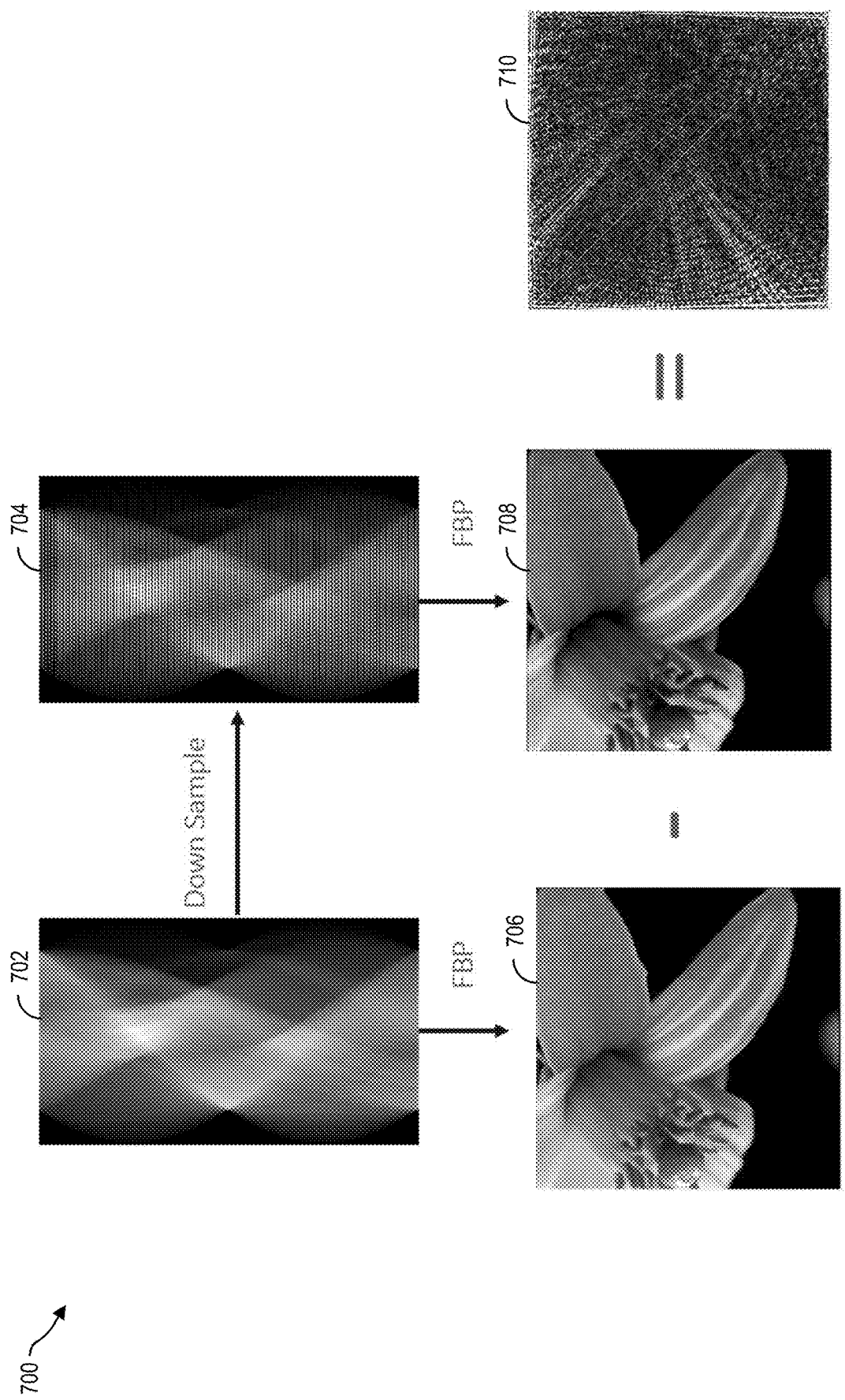
FIG. 7 illustrates an exemplary process for generating streak residuals from CT measurement data.
Figure 8:
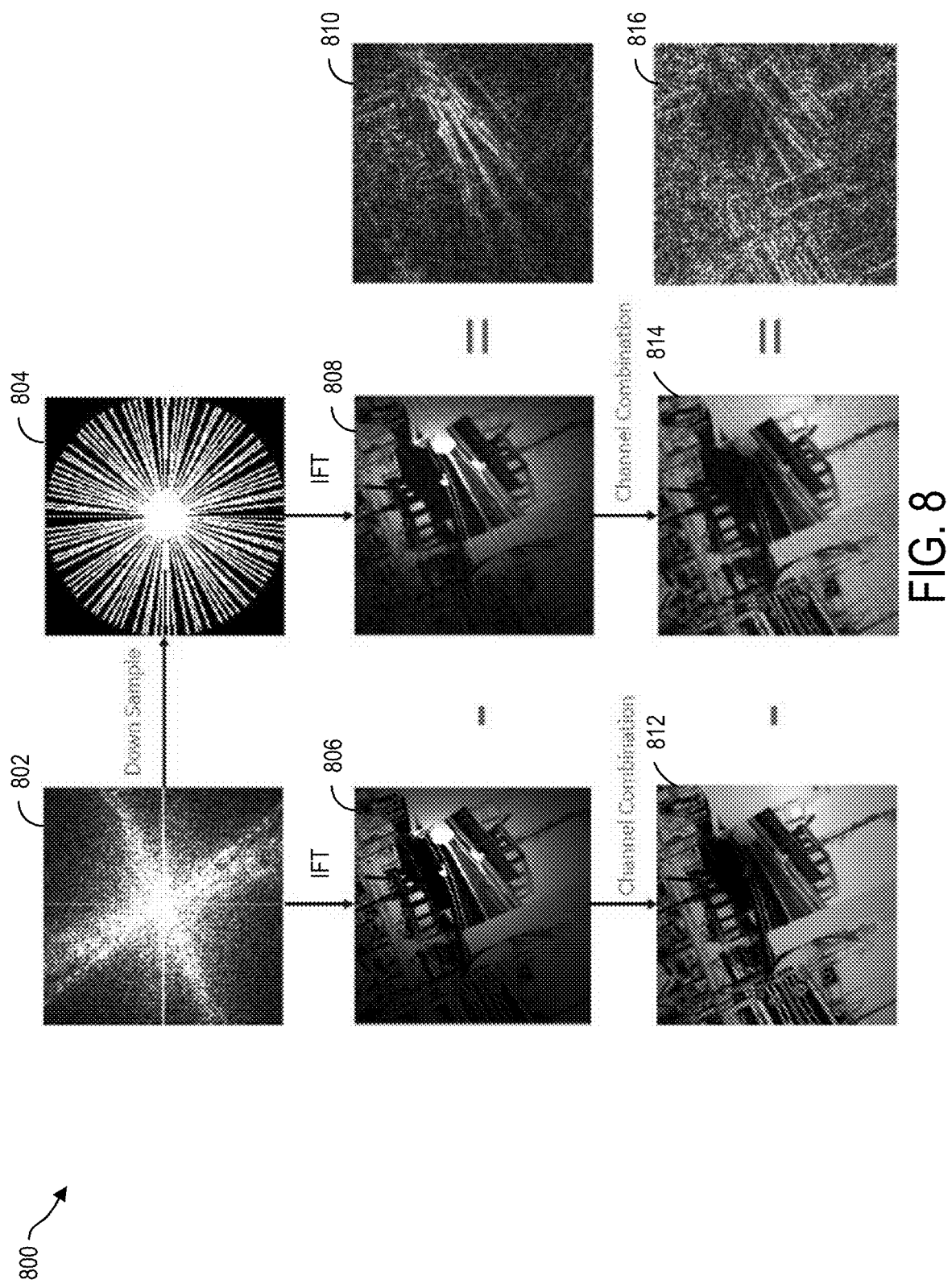
FIG. 8 illustrates an exemplary process for generating streak residuals from MRI measurement data.
Figure 9:
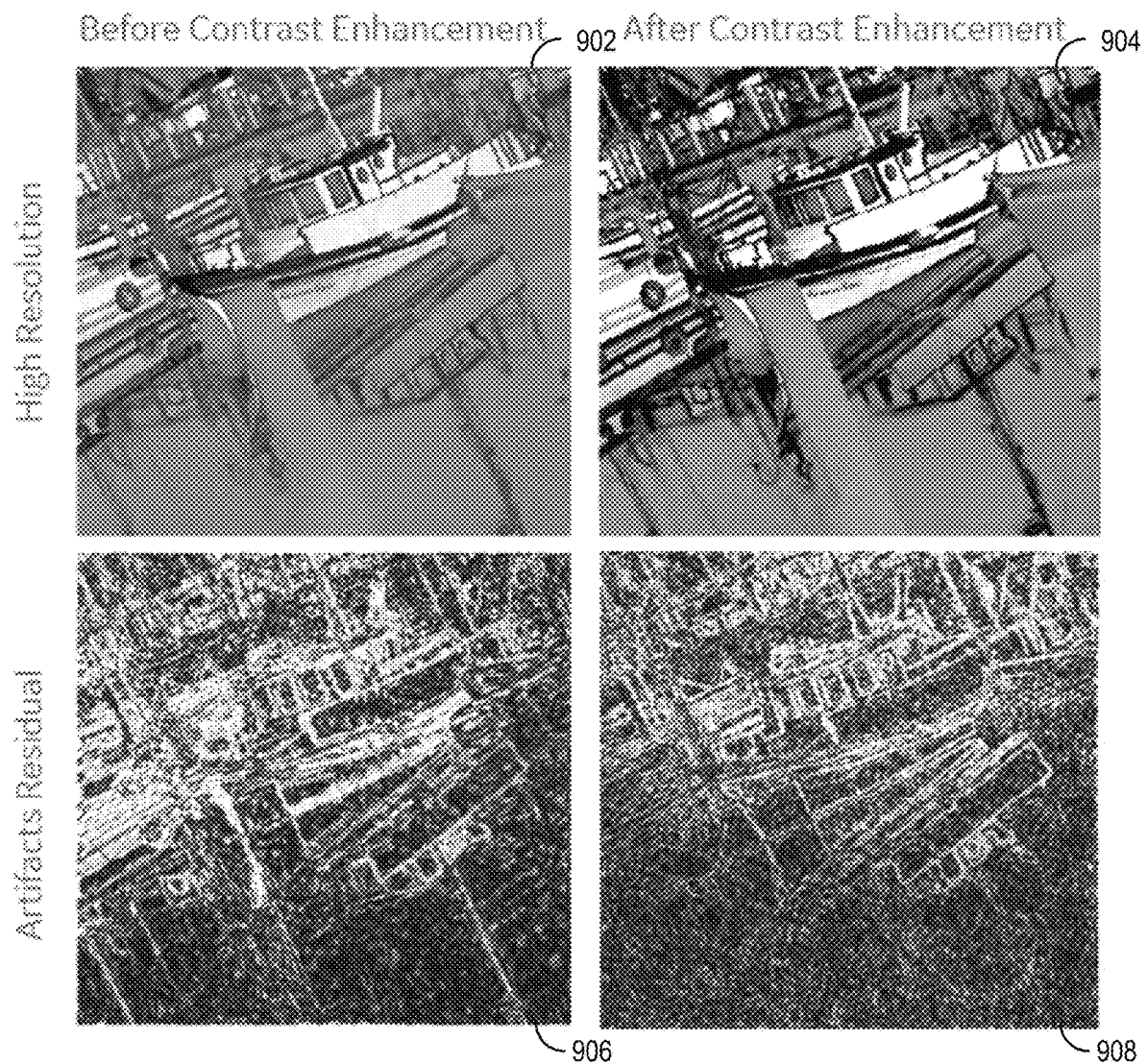
FIG. 9 shows a comparison between a first streak residual generated without contrast enhancement, and a second streak residual generated with contrast enhancement.
Figure 10:
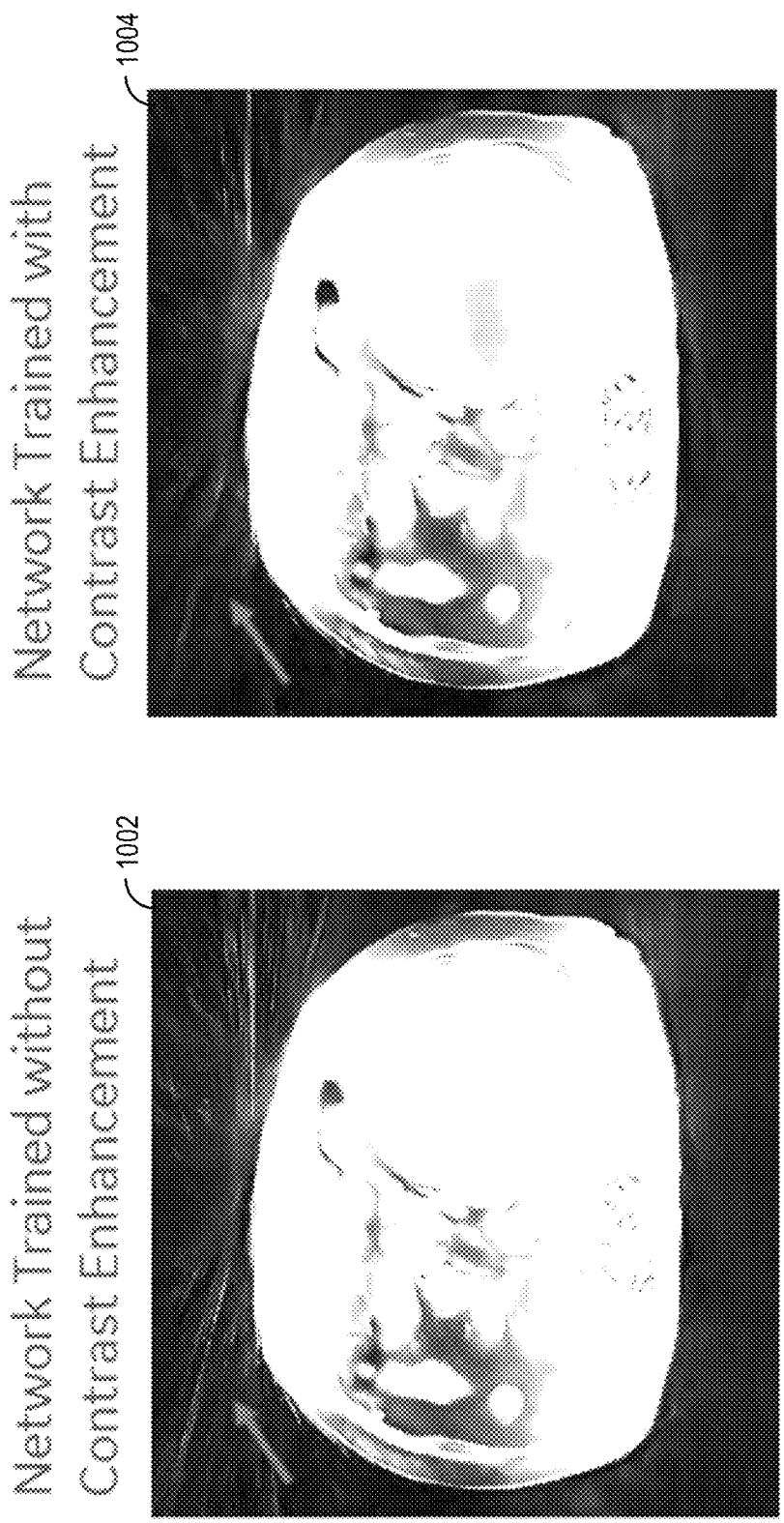
FIG. 10 shows a comparison between a first de-noised medical image, de-noised using a deep neural network trained on training data generated without contrast enhancement, and a second de-noised medical image, de-noised using a deep neural network trained on training data generated with contrast enhancement.

FIG. 7 illustrates an exemplary process by which a streak residual may be produced from CT measurement data (sinogram data), whereas FIG. 8 illustrates an exemplary process by which streak residuals may be produced from MRI measurement data (k-space data). Further, FIG. 9 shows a comparison between streak residuals produced from contrast enhanced images, and non-contrast enhanced medical images, illustrating the impact of contrast enhancement on streak residual generation. Likewise, FIG. 10 shows a comparison between a first de-noised medical image 1002 produced by a deep neural network trained on training data triads generated without contrast enhancement, and a second de-noised medical image 1004 produced by a deep neural network trained on training data triads generated with contrast enhancement.

As used herein, the term de-noised medical image may refer to an image devoid of streak artifacts and noise, or to an image comprising a substantially reduced intensity of streak artifacts and noise relative to an initially acquired and reconstructed image. In some instances, the term partially de-noised image may be used to denote an image comprising a relatively lower intensity or amount of streak artifacts and noise and noise than a corresponding, un-processed image. As used herein, the terms streaky-noisy image will be understood to refer to an image comprising both streak artifacts and noise.

Turning first to FIG. 1, MRI system 10 is shown. MRI system 10 includes a magnetostatic field magnet unit 12, a gradient coil unit 13, a local RF coil unit 14, an RF body or volume coil unit 15, a transmit/receive (T/R) switch 20, an RF driver unit 22, a gradient coil driver unit 23, a data acquisition unit 24, a controller unit 25, a patient table or bed 26, an image processing system 31, a user input device 32, and a display device 33. RF coils are used to transmit RF excitation signals ("transmit coil"), and to receive the MR signals emitted by an imaging subject ("receive coil"). In some embodiments, the RF coil unit 14 is a surface coil, which is a local coil typically placed proximate to the anatomy of interest of a subject 16. Herein, the RF body coil unit 15 is a transmit coil that transmits RF signals, and the local RF coil unit 14 receives the MR signals. As such, the transmit body coil (e.g., RF body coil unit 15) and the surface receive coil (e.g., RF coil unit 14) are separate but electromagnetically coupled components. The MRI system 10 transmits electromagnetic pulse signals to the subject 16 placed in an imaging space 18 with a static magnetic field formed to perform a scan for obtaining magnetic resonance signals from the subject 16. One or more MR images of the subject 16 can be reconstructed based on the magnetic resonance signals thus obtained by the scan.

The magnetostatic field magnet unit 12 includes, for example, an annular superconducting magnet, which is mounted within a toroidal vacuum vessel. The magnet defines a cylindrical space surrounding the subject 16 and generates a constant primary magnetostatic field Bo.

The MRI system 10 also includes a gradient coil unit 13 that forms a gradient magnetic field in the imaging space 18 so as to provide the magnetic resonance signals received by the RF coil arrays with three-dimensional positional information. The gradient coil unit 13 includes three gradient coil systems, each of which generates a gradient magnetic field along one of three spatial axes perpendicular to each other, and generates a gradient field in each of a frequency encoding direction, a phase encoding direction, and a slice selection direction in accordance with the imaging condition. More specifically, the gradient coil unit 13 applies a gradient field in the slice selection direction (or scan direction) of the subject 16, to select the slice; and the RF body coil unit 15 or the local RF coil arrays may transmit an RF pulse to a selected slice of the subject 16. The gradient coil unit 13 also applies a gradient field in the phase encoding direction of the subject 16 to phase encode the magnetic resonance signals from the slice excited by the RF pulse. The gradient coil unit 13 also applies a gradient field in the frequency encoding direction of the subject 16 to frequency encode the magnetic resonance signals from the slice excited by the RF pulse.

The RF coil unit 14 is disposed, for example, to enclose the region to be imaged of the subject 16. In some examples, the RF coil unit 14 may be a receive coil. In the static magnetic field space or imaging space 18 where a static magnetic field Bo is formed by the magnetostatic field magnet unit 12, the RF coil unit 15 transmits, based on a control signal from the controller unit 25, an RF pulse that is an electromagnet wave to the subject 16 and thereby generates a high-frequency magnetic field, Bi. This excites a spin of protons in the slice to be imaged of the subject 16. The RF coil unit 14 receives, as a magnetic resonance signal, the electromagnetic wave generated when the proton spin thus excited in the slice to be imaged of the subject 16 returns into alignment with the initial magnetization. In some embodiments, the RF coil unit 14 may transmit the RF pulse and receive the MR signal. In other embodiments, the RF coil unit 14 may only be used for receiving the MR signals, but not transmitting the RF pulse.

The RF body coil unit 15 is disposed, for example, to enclose the imaging space 18, and produces RF magnetic field pulses orthogonal to the main magnetic field Bo produced by the magnetostatic field magnet unit 12 within the imaging space 18 to excite the nuclei. In contrast to the RF coil unit 14, which may be disconnected from the MRI system 10 and replaced with another RF coil unit, the RF body coil unit 15 is fixedly attached and connected to the MRI system 10. Furthermore, whereas local coils such as the RF coil unit 14 can transmit to or receive signals from only a localized region of the subject 16, the RF body coil unit 15 generally has a larger coverage area. The RF body coil unit 15 may be used to transmit or receive signals to the whole body of the subject 16, for example. Using receive-only local coils and transmit body coils provides a uniform RF excitation and good image uniformity at the expense of high RF power deposited in the subject. For a transmit-receive local coil, the local coil provides the RF excitation to the region of interest and receives the MR signal, thereby decreasing the RF power deposited in the subject. It should be appreciated that the particular use of the RF coil unit 14 and/or the RF body coil unit 15 depends on the imaging application.

The T/R switch 20 can selectively electrically connect the RF body coil unit 15 to the data acquisition unit 24 when operating in receive mode, and to the RF driver unit 22 when operating in transmit mode. Similarly, the T/R switch 20 can selectively electrically connect the RF coil unit 14 to the data acquisition unit 24 when the RF coil unit 14 operates in receive mode, and to the RF driver unit 22 when operating in transmit mode. When the RF coil unit 14 and the RF body coil unit 15 are both used in a single scan, for example if the RF coil unit 14 is configured to receive MR signals and the RF body coil unit 15 is configured to transmit RF signals, then the T/R switch 20 may direct control signals from the RF driver unit 22 to the RF body coil unit 15 while directing received MR signals from the RF coil unit 14 to the data acquisition unit 24. The coils of the RF body coil unit 15 may be configured to operate in a transmit-only mode or a transmit-receive mode. The coils of the local RF coil unit 14 may be configured to operate in a transmit-receive mode or a receive-only mode.

The RF driver unit 22 includes a gate modulator (not shown), an RF power amplifier (not shown), and an RF oscillator (not shown) that are used to drive the RF coils (e.g., RF coil unit 15) and form a high-frequency magnetic field in the imaging space 18. The RF driver unit 22 modulates, based on a control signal from the controller unit 25 and using the gate modulator, the RF signal received from the RF oscillator into a signal of predetermined timing having a predetermined envelope. The RF signal modulated by the gate modulator is amplified by the RF power amplifier and then output to the RF coil unit 15.

The gradient coil driver unit 23 drives the gradient coil unit 13 based on a control signal from the controller unit 25 and thereby generates a gradient magnetic field in the imaging space 18. The gradient coil driver unit 23 includes three systems of driver circuits (not shown) corresponding to the three gradient coil systems included in the gradient coil unit 13.

The data acquisition unit 24 includes a pre-amplifier (not shown), a phase detector (not shown), and an analog/digital converter (not shown) used to acquire the magnetic resonance signals received by the RF coil unit 14. In the data acquisition unit 24, the phase detector phase detects, using the output from the RF oscillator of the RF driver unit 22 as a reference signal, the magnetic resonance signals received from the RF coil unit 14 and amplified by the pre-amplifier, and outputs the phase-detected analog magnetic resonance signals to the analog/digital converter for conversion into digital signals. The digital signals thus obtained are output to the image processing system 31.

The MRI system 10 includes a table 26 for placing the subject 16 thereon. The subject 16 may be moved inside and outside the imaging space 18 by moving the table 26 based on control signals from the controller unit 25.

The controller unit 25 includes a computer and a recording medium on which a program to be executed by the computer is recorded. The program when executed by the computer causes various parts of the system to carry out operations corresponding to pre-determined scanning. The recording medium may comprise, for example, a ROM, flexible disk, hard disk, optical disk, magneto-optical disk, CD-ROM, or non-transitory memory card. The controller unit 25 is connected to the user input device 32 and processes the operation signals input to the user input device 32 and furthermore controls the table 26, RF driver unit 22, gradient coil driver unit 23, and data acquisition unit 24 by outputting control signals to them. The controller unit 25 also controls, to obtain a desired image, the image processing system 31 and the display device 33 based on operation signals received from the user input device 32.

The user input device 32 includes user input devices such as a touchscreen, keyboard, and a mouse. The user input device 32 is used by an MRI system operator, for example, to input such data as an imaging protocol, to accept or decline a scan region preview, and in some embodiments, to set a region where an imaging sequence is to be executed. The imaging protocol data, the scan region preview acceptance or declination, and the imaging sequence execution region are output to the controller unit 25.

The image processing system 31 includes a processor and non-transitory memory on which machine executable instructions may be stored, wherein the machine executable instructions may enable the processor to execute one or more of the steps of one or more of the methods herein disclosed. The image processing system 31 may be connected to the controller unit 25 and may perform data processing based on control signals received from the controller unit 25 or user input device 32. The image processing system 31 is also connected to the data acquisition unit 24 and generates spectrum data by applying various image processing operations to the magnetic resonance signals output from the data acquisition unit 24.

MRI system 10 may acquire diagnostic images according to one or more imaging protocols. In some embodiments, imaging protocols may indicate one or more k-space sampling patterns, and/or one or more k-space sampling densities, used to acquire k-space data, wherein the k-space data may be reconstructed to form a medical image according to one or more methods of image reconstruction known in the art. In one embodiment, MRI system 10 may include instructions stored in non-transitory memory, that when executed, cause the MRI system 10 to acquire k-space data according to one or more pre-determined k-space sampling patterns. In some embodiments, MRI system 10 may be configured to acquire measurement data/k-space data by executing a PROPELLER imaging protocol, wherein one or more blades of k-space, centered on a k-space origin, may be acquired. In some embodiments, the MRI system 10 may be configured to acquire MRI measurement data using a stack-of-stars imaging protocol. Further, in some embodiments, MRI system 10 may be configured to acquire measurement data using a reduced k-space sampling density (also referred to as an undersampling pattern), wherein at least part of the k-space is sampled with reduced density, thereby reducing acquisition time.

The display device 33 may display an image on a display screen of the display device 33 based on control signals received from the controller unit 25. The display device 33 displays, for example, a de-noised medical image. Display device 33 may comprise a graphical user interface (GUI), wherein a user may interact with/input/alter one or more data fields via user input device 32. In one embodiment, display device 33 may display a GUI comprising input fields/slide-bars configured to enable a user to adjust a first extent of streak residual removal and a second extent of noise residual removal from an acquired MRI image. The display device 33 may display two-dimensional (2D) images, three-dimensional (3D) images, and/or four-dimensional images (a 3D image through time) of the subject 16 generated by the image processing system 31.

During a scan, RF coil array interfacing cables (not shown in FIG. 1) may be used to transmit signals between the RF coils (e.g., RF coil unit 14 and RF body coil unit 15) and other aspects of the processing system (e.g., data acquisition unit 24, controller unit 25, and so on), for example to control the RF coils and/or to receive information from the RF coils.

Figure 2:
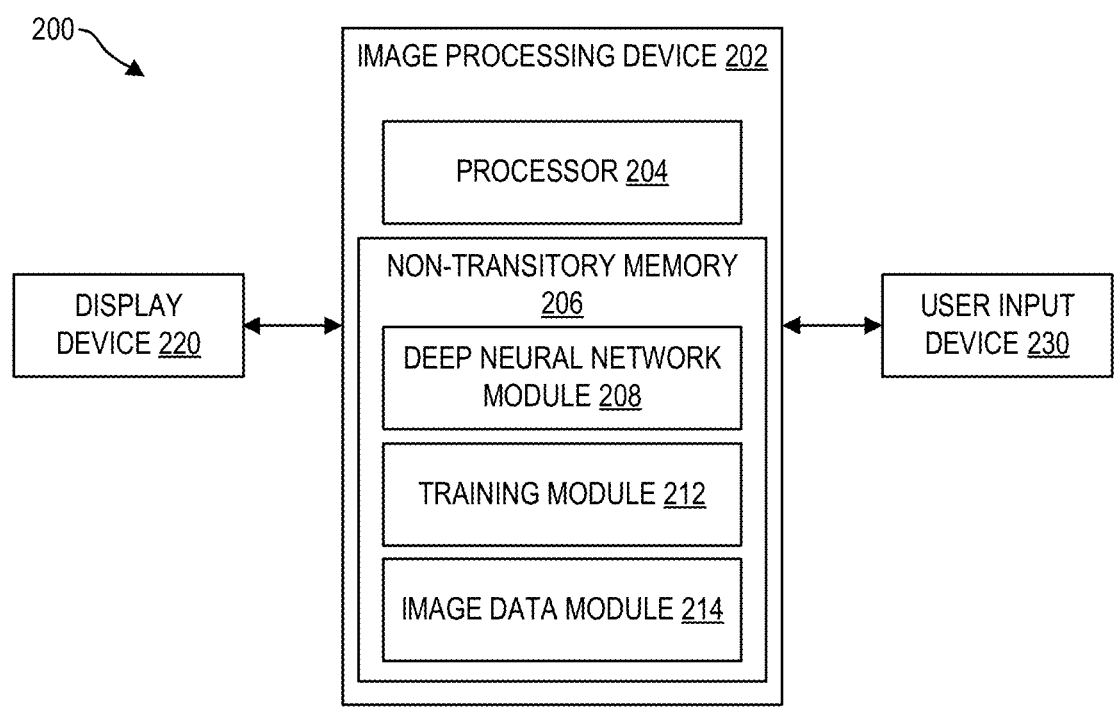
FIG. 2 shows an image processing device, which may be used to selectively remove streak artifacts and noise from medical images.

Referring now to FIG. 2, image processing system 200 is shown, in accordance with an exemplary embodiment. In some embodiments, image processing system 200 is incorporated into the MRI system 10. In some embodiments, at least a portion of image processing system 200 is disposed at a device (e.g., edge device, server, etc.) communicably coupled to the MRI system 10 via wired and/or wireless connections. In some embodiments, at least a portion of the image processing system 200 is disposed at a device (e.g., a workstation), located remote from the MRI system 10, which is configured to receive images from the MRI system 10 or from a storage device configured to store images acquired by the MRI system 10. Image processing system 200 may comprise image processing device 202, user input device 230, and display device 220. In some embodiments, image processing system 200 may receive CT images from a CT imaging system, wherein the image processing system 200 may be communicably coupled via wired or wireless connection to one or more CT imaging systems. In some embodiments, image processing device 202 may be communicably coupled to both an MRI imaging system and a CT imaging system, and may be configured to receive and process both MRI images and CT images. In some embodiments, image processing device 202 may be communicably coupled to a picture archiving and communication system (PACS), and may receive images from, and/or send images to, the PACS.

Image processing device 202 includes a processor 204 configured to execute machine readable instructions stored in non-transitory memory 206. Processor 204 may be single core or multi-core, and the programs executed thereon may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration.

Non-transitory memory 206 may store deep neural network module 208, training module 212, and image data 214. Deep neural network module 208 may include one or more deep neural networks, comprising a plurality of weights and biases, activation functions, pooling functions, and instructions for implementing the one or more deep neural networks to identify and extract features within a medical image of interest, and to map the extracted features to a streak residual and a noise residual, corresponding to streak artifacts and noise within the medical image of interest, respectively. In some embodiments, deep neural network module 208 may comprise one or more trained deep neural networks, such as deep neural network 324, and may implement the trained deep neural network according to one or more operations of method 400, to selectively remove streak artifacts and noise, based on identified features in the image.

Deep neural network module 208 may include trained and/or un-trained deep neural networks. In some embodiments, the deep neural network module 208 is not disposed at the image processing device 202, but is disposed at a remote device communicably coupled with image processing device 202 via wired or wireless connection. Deep neural network module 208 may include various deep neural network metadata pertaining to the trained and/or un-trained networks. In some embodiments, the deep neural network metadata may include an indication of the training data used to train a deep neural network, a training method employed to train a deep neural network, and an accuracy/validation score of a trained deep neural network. In some embodiments, deep neural network module 208 may include metadata for a trained deep neural network indicating a type of anatomy, and/or a type of imaging modality, to which the trained deep neural network may be applied.

Non-transitory memory 206 further includes training module 212, which comprises machine executable instructions for training one or more of the deep neural networks stored in deep neural network module 208. In some embodiments, training module 212 may include instructions for generating training data triads by executing one or more operations of method 500, and utilizing said training data triads according to one or more operations of method 600 to train a deep neural network to identify streak artifacts and noise within a medical image, and map the streak artifacts and noise to a streak residual and a noise residual, respectively. In one embodiment, the training module 212 may include gradient descent algorithms, loss functions, and machine executable rules for generating and/or selecting training data for use in training a deep neural network. Training module 212 may further include instructions, that when executed by processor 204, cause image processing device 102 to train a deep neural network by executing one or more of the operations of method 600, discussed in more detail below with reference to FIG. 6. In some embodiments, the training module 212 is not disposed at the image processing device 202, but is disposed remotely, and is communicably coupled with image processing device 202.

Non-transitory memory 206 may further include image data module 214, comprising images/imaging data acquired by one or more imaging devices, such as MRI system 10. The images stored in image data 214 may comprise medical images from various imaging modalities or from various makes/models of medical imaging devices, and may comprise images of various views of anatomical regions of one or more patients. In some embodiments, medical images stored in image data module 214 may include information identifying an imaging modality and/or an imaging device (e.g., model and manufacturer of an imaging device) by which the medical image was acquired. In some embodiments, images stored in image data module 214 may include metadata indicating one or more acquisition parameters used to acquire said images. In one example, metadata for the images may be stored in DICOM headers of the images. In some embodiments, the metadata may include a k-space sampling pattern and a k-space sampling density used to acquire the images. In some embodiments, the metadata may indicate a number of projections acquired in a CT imaging protocol, and may further indicate angles of acquisition for each of the projections. In some embodiments, image data module 214 may comprise x-ray images acquired by an x-ray device, MR images captured by an MRI system, CT images captured by a CT imaging system, PET images captured by a PET system, and/or one or more additional types of medical images.

In some embodiments, the non-transitory memory 206 may include components disposed at two or more devices, which may be remotely located and/or configured for coordinated processing. In some embodiments, one or more aspects of the non-transitory memory 206 may include remotely-accessible networked storage devices configured in a cloud computing configuration.

Image processing system 200 may further include user input device 230. User input device 230 may comprise one or more of a touchscreen, a keyboard, a mouse, a trackpad, a motion sensing camera, or other device configured to enable a user to interact with and manipulate data within image processing system 200. In some embodiments, user input device 230 enables a user to adjust an extent of streak residual removal and an extent of noise residual removal. In some embodiments, a user may input or select a first value indicating an extent of streak residual removal, the user may further input or select a second value indicating an extent of noise residual removal, and the image processing device 202 may respond to receiving the user input and independently by adjusting an extent of streak residual removal and an extent of noise residual removal based on said user input, to produce a partially de-noised medical image.

Display device 220 may include one or more display devices utilizing virtually any type of technology. In some embodiments, display device 220 may comprise a computer monitor. Display device 220 may be configured to receive data from image processing device 202, and to display de-noised, partially de-noised, or non-de-noised medical images based on the received data. Display device 220 may be combined with processor 204, non-transitory memory 206, and/or user input device 230 in a shared enclosure, or may be a peripheral display device and may comprise a monitor, touchscreen, projector, or other display device known in the art, which may enable a user to view images, and/or interact with various data stored in non-transitory memory 206.

It should be understood that image processing system 200 shown in FIG. 2 is for illustration, not for limitation. Another appropriate image processing system may include more, fewer, or different components.

Figure 3:
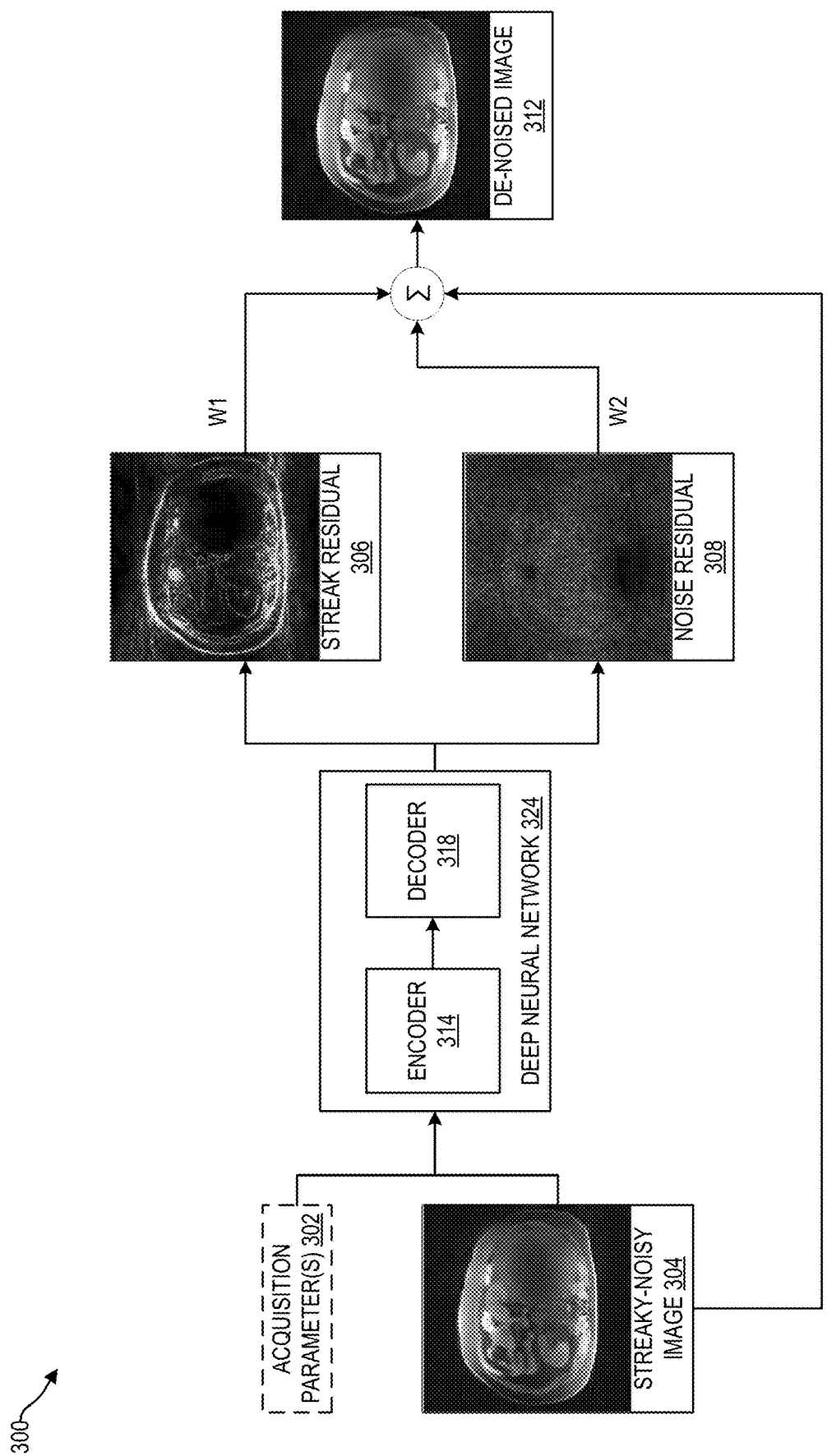
FIG. 3 shows an example of a system employing a trained deep neural network to infer a streak residual and a noise residual for a streaky-noisy image.

Turning to FIG. 3, a box diagram of a system 300, for mapping streaky-noisy images, to de-noised medical images, using a deep neural network is shown. System 300 may be implemented by an image processing device, such as image processing device 202, or other appropriately configured computing systems. System 300 shows an exemplary streaky-noisy image 304, mapped to an exemplary streak residual 306 and an exemplary noise residual 308, via deep neural network 324. The streak residual 306 and the noise residual 308 are then weighted (via W1 and W2, respectively) and subtracted from streaky-noisy image 304 to produce de-noised image 312. As used herein, the term streaky-noisy may refer to an image comprising both streak artifacts and noise.

Streaky-noisy image 304 may comprise a plurality of pixel/voxel intensity values, and may be a 2D or a 3D image. Streaky-noisy image 304 may comprise an MRI image or a CT image. In some embodiments, streaky-noisy image 304 may comprise an MRI image acquired via undersampling of k-space, such as via a radial sampling pattern. In some embodiments, streaky-noisy image 304 may comprise a CT image acquired via undersampled sinogram data.

Acquisition parameters 302 may comprise one or more pieces of contextual data pertaining to streaky-noisy image 304. In some embodiments, acquisition parameters 302 include a k-space sampling pattern used to acquire streaky-noisy image 304. In some embodiments, acquisition parameters 302 comprise a k-space sampling density used to acquire streaky-noisy image 304. In some embodiments, acquisition parameters 302 may include an indication of the number and orientation of x-ray projections used to construct streaky-noisy image 304.

Deep neural network 324 may comprise an encoding portion (e.g., encoder 314), and a decoding portion (decoder 318), wherein the encoder 314 is configured to identify and extract features from input images, such as streaky-noisy image 304, and wherein the decoder 318 is configured to map the extracted features output by the encoder 314 to a corresponding streak residual (e.g., streak residual 306) and a corresponding noise residual (e.g., noise residual 308). In some embodiments, separate deep neural networks may be used to produce streak residuals and noise residuals.

Deep neural network 324 may be configured to receive data from streaky-noisy image 304, via an input layer, and may optionally receive acquisition parameters 302. In some embodiments, the input layer may comprise a first plurality of nodes/neurons configured to receive pixel/voxel intensity data from streaky-noisy image 304. Optionally, the input layer may comprise a second plurality of nodes/neurons configured to receive acquisition parameters 302. In some embodiments, acquisition parameters 302 may be concatenated with or embedded in streaky-noisy image 304, and both streaky-noisy image 304 and acquisition parameters 302 may be received by the first plurality of nodes/neurons. Data received by the input layer may be passed to encoder 314.

Encoder 314 may comprise a first plurality of layers/feature maps, configured to identify and extract features embedded within streaky-noisy image 304. Each feature map may receive input from a file or a previous feature map, and may transform/map the received input to output to produce a next feature map. In some embodiments, said transformation may comprise convolutions using learned filters, pooling, activation functions (including rectified linear units), etc. Each feature map may comprise a plurality of neurons, where in some embodiments, each neuron may receive input from a subset of neurons of a previous layer/feature map, and may compute a single output based on the received inputs, wherein the output may be propagated to a subset of the neurons in a next layer/feature map. In some embodiments, the neurons of the feature maps may compute an output by performing a dot product of received inputs using a set of learned weights (each set of learned weights may herein be referred to as a filter), wherein each received input has a distinct corresponding learned weight, wherein the learned weight was learned during training phase. The weights (and biases) of deep neural network 324 may be learned during training, as will be discussed in more detail below, with reference to FIGS. 5 and 6. Output from encoder 314, which may comprise a plurality of identified and extracted features, is passed to decoder 318.

Decoder 318 may comprise a second plurality of layers/features maps, analogous to encoder 314. Each feature map may receive input from a previous feature map (or from encoder 314), and may transform/map the received input to output to produce a next feature map. In some embodiments, said transformation may comprise up-convolutions using learned deconvolution filters, activation functions (including rectified linear units), etc. Each feature map may comprise a plurality of neurons, where in some embodiments, each neuron may receive input from a subset of neurons of a previous layer/feature map, and may compute a single output based on the received inputs, wherein the output may be propagated to a subset of the neurons in a next layer/feature map. In some embodiments, the neurons of the feature maps may compute an output by performing a dot product of received inputs using a set of learned weights (each set of learned weights may herein be referred to as a filter), wherein each received input has a distinct corresponding learned weight, wherein the learned weight was learned during training phase. Decoder 318 may further include one or more fully connected layers, wherein each node of a previous layer is connected to each node of a current layer.

Deep neural network 324 may further comprise an output layer, configured to output both a streak residual, such as streak residual 306, and a noise residual, such as noise residual 308. In some embodiments, the output layer comprises a first plurality of neurons configured to produce streak residual 306 based on input received from decoder 318, and a second plurality of neurons configured to produce noise residual 308 based on input received from decoder 318. Each neuron of the output layer may correspond to a pixel/voxel of the streak residual 306 or the noise residual 308. The dimensions of the streak residual 306 and the noise residual 308 may match the dimensions of streaky-noisy image 304. As an example, the output of a neuron of the output layer may indicate a streak artifact intensity (or a noise intensity) in a corresponding region of streaky-noisy image 304. Said another way, streak residual 306 may comprise a map of the spatial distribution and intensity of streak artifacts present in streaky-noisy image 304, while noise residual 308 may comprise a map of the spatial distribution and intensity of noise present in streaky-noisy image 304.

It should be understood that the architecture and configuration of deep neural network 324 is for illustration, not for limitation. Any appropriate neural network can be used herein for inferring streak residuals and noise residuals MR and/or CT images, including U-nets, ResNets, recurrent neural networks, General Regression Neural Network (GRNN), etc. One or more specific embodiments of the present disclosure are described above in order to provide a thorough understanding. However, these described embodiments are only examples of systems and methods for separately inferring streak residuals and noise in images using a deep neural network. The skilled artisan will understand that specific details described in the embodiments can be modified when being placed into practice without deviating the spirit of the present disclosure.

Streak residual 306 and noise residual 308 may be weighted, as indicated by W1 and W2, shown in FIG. 3. In one embodiment, each pixel/voxel value of streak residual 306 may be multiplied by W1 (a first extent) to produce a first weighted streak residual, and similarly, each pixel/voxel value of noise residual 308 may be multiplied by W2 (a second extent) to produce a weighted noise residual. The weighted streak residual and the weighted noise residual may then be subtracted from the streaky-noisy image 304, to remove streak artifacts and noise present in streaky-noisy image 304 to a first extent and a second extent, respectively, to produce de-noised image 312 (as indicated by the circle enclosed Σ). As the streak residual 306 comprises a map of the streak artifacts present in streaky-noisy image 304, and as noise residual 308 comprises the noise present in streaky-noisy image 304, system 300 is able to remove the streak artifacts and the noise substantially or to a given extent (e.g., from 0% to 100% removal). Further, system 300 may independently select extents of streak artifact removal and noise removal (e.g., streak artifact removal may be set to 50% by setting W1 to 0.5, and noise removal may be set to 95% by setting W2 to 0.95).

Turning to FIG. 4, a flowchart of an example method 400 for removing streak artifacts and noise from streaky-noisy images using trained deep neural networks is shown. Method 400 may be executed by one or more of the systems discussed above. In one embodiment, image processing device 202, implementing system 300, may execute one or more operations of method 400.

At operation 402, the image processing device receives a streaky-noisy image, such as streaky-noisy image 420. In some embodiments, the streaky-noisy image may comprise a 2D or 3D image of an anatomical region of a patient, comprising a 2D array of pixel intensity values in one or more channels or a 3D array of voxel intensity values in one or more channels. In some embodiments, the streaky-noisy image comprises an MR image acquired by an MRI system, such as MRI system 10, of an anatomical region of a patient. In some embodiments, the streaky-noisy image comprises a computed tomography (CT) image of an anatomical region of a patient acquired by a CT imaging system. In some embodiments, the received streaky-noisy image may include one or more pieces of metadata, wherein one or more acquisition parameters may be stored. In some embodiments, the metadata may be included in a DICOM header of the received streaky-noisy image. Said image metadata may include one or more of a k-space sampling pattern and/or k-space sampling density used during acquisition of the image, a sinogram sampling pattern and/or a sinogram sampling density, an indication of a reconstruction algorithm used to reconstruct the image from measurement data, etc.

At operation 404, the image processing device selects a trained deep neural network. In some embodiments, the image processing device may select a trained deep neural network from amongst a plurality of trained deep neural networks, based on one or more pieces of metadata pertaining to the trained deep neural network, and further based on one or more pieces of metadata included with the received medical image. In some embodiments, the image processing device may compare a first piece of metadata included with the received streaky-noisy image with a plurality of pieces of metadata pertaining to the deep neural network, and may select the trained deep neural network in response to said first piece of metadata matching one or more pieces of metadata of the plurality of pieces of metadata pertaining to the trained deep neural network. In some embodiments, said first piece of metadata may comprise an indication of an imaging protocol used to acquire the streaky-noisy image, wherein said imaging protocol may indicate one or more acquisition parameters used by an imaging device to acquire the streaky-noisy image.

In some embodiments, operation 404 includes the image processing device accessing a location of non-transitory memory, wherein an index of a plurality of trained deep neural networks is stored, and comparing one or more pieces of metadata associated with the streaky-noisy image against one or more indexing parameters of the plurality of deep neural networks. In some embodiments, the image processing device may select a deep neural network based on a type of training data used to train the deep neural network. In some embodiments, a deep neural network may be trained to identify streak residuals and noise residuals in images acquired using one or more pre-determined acquisition parameters (e.g., k-space sampling density, k-space sampling pattern, sinogram sampling density, sinogram sampling pattern, echo sequence, etc.), and the deep neural network may be indexed based on the pre-determined acquisition parameters. In such embodiments, operation 404 may include the image processing device comparing one or more image acquisition parameters used to acquire a streaky-noisy image to be de-noised, stored in metadata associated with said image, against metadata pertaining to a trained deep neural network indicating acquisition parameters of images used to train the deep neural network.

At operation 406, the image processing device maps the streaky-noisy image to a streak residual (e.g., streak residual 422) and a noise residual (e.g., noise residual 424) using the trained deep neural network. Optionally, operation 406 may include the image processing device receiving one or more acquisition parameters pertaining to acquisition of the streaky-noisy image, inputting the streaky-noisy image and the one or more acquisition parameters into an input layer of the trained deep neural network, and mapping the medical image and the one or more acquisition parameters to the streak residual and the noise residual using the trained deep neural network, as described in more detail with reference to FIG. 3, above.

At operation 408, the image processing device removes the streak residual from the streaky-noisy image to a first extent and removes the noise residual from the streaky-noisy image to a second extent, to produce a de-noised image. In some embodiments, the first extent comprises a first value between 0 and 1 (and any fractional amount therebetween), inclusive, and wherein the second extent comprises a second value between 0 and 1 (and any fractional amount therebetween), inclusive. In other words, intensity of the streak residual and the noise residual may be independently removed to varying extents, in the range of 0% to 100%. In some embodiments, a user may pre-select a preferred first extent and a preferred second extent, and said first extent and said second extent may be stored in a location of non-transitory memory associated with user preferences, in such embodiments, the image processing device may, at operation 408, access the location in non-transitory memory and retrieve the pre-determined first extent and second extent. In some embodiments, if a user has not pre-selected a preferred first extent and a preferred second extent, the image processing device may, at operation 408, access a default first extent and a default second extent. In some embodiments, the image processing device may include instructions for intelligently selecting a first extent and a second extent based on the input streaky-noisy image and one or more pieces of metadata associated therewith.

In some embodiments, the streak residual comprises a 2D or 3D array of intensity values, representing the intensity of streak artifacts identified by the trained deep neural network, and operation 408 comprises multiplying the 2D or 3D array of streak intensity values by a first weighting factor (also referred to herein as W1), to produce a weighted streak residual comprising a plurality of weighted streak intensity values. The weighted streak residual may be subtracted from the streaky-noisy image by performing pixel-wise/voxel-wise subtraction of weighted streak intensity values of the weighted streak residual from intensity values of the streaky-noisy image, e.g., by subtracting a weighted streak intensity value from a first pixel of the weighted streak residual from an intensity value of a second pixel of the streaky-noisy image, wherein the first pixel and the second pixel represent a same region of an imaged space.

Likewise, in some embodiments, the noise residual comprises a 2D or 3D array of intensity values, representing the intensity of noise identified by the trained deep neural network, and operation 408 comprises multiplying the 2D or 3D array of noise intensity values by a second weighting factor (also referred to herein as W2), to produce a weighted noise residual comprising a plurality of weighted noise intensity values. The weighted noise residual may be subtracted from the streaky-noisy image by performing pixel-wise/voxel-wise subtraction of weighted noise intensity values of the weighted noise residual from intensity values of the streaky-noisy image, e.g., by subtracting a weighted noise intensity value of a first pixel of the weighted noise residual from an intensity value of a second pixel of the streaky-noisy image, wherein the first pixel and the second pixel represent a same region of an imaged space.

In some embodiments, operation 408 includes the image processing device retrieving W1 and W2 from a pre-determined location in non-transitory memory. In some embodiments, the pre-determined location in non-transitory memory comprises a user preferences file configured by a user, wherein the user preferences file may include a user selected W1 and W2. In some embodiments, W1 and W2 may be set to 1.0 and 1.0, respectively, indicating 100% removal of both streak artifacts and noise. In some embodiments, W1 and W2 may be set independently to values other than 1.0. Turning briefly to FIG. 11, a comparison between an exemplary streaky-noisy image 1102 and an exemplary de-noised medical image, is shown. As can be seen in FIG. 11, streaky-noisy image 1102 comprises a plurality of streak artifacts (elongated regions of higher intensity extending beyond portions of anatomy)

At operation 410, the image processing device displays the de-noised medical image. An example of a de-noised medical image 426 is shown to the left of operation 412 in FIG. 4. In some embodiments, operation 410 includes displaying an indication of the extent of removal of the streak residual and an indication of the extent of removal of the noise removal. In some embodiments, operation 410 includes displaying the first extent, W1, to which the streak residual was removed, and displaying the second extent, W2, to which the noise residual was remove, along with a GUI configured to receive user input for adjusting the first extent W1 and/or adjusting the second extent W2.

At operation 412, method 400 optionally includes the image processing device adjusting the first extent and the second extent based on user input received via a user input device, to produce a third extent and a fourth extent. In some embodiments, a user may input a third extent and a fourth extent into the image processing device using a user input device, and at operation 412, the image processing device may replace the first extent with the third extent, and may replace the second extent with the fourth extent. In some embodiments, at operation 412, the image processing device may receive a first scaling factor and a second scaling factor, and may adjust the first extent to produce the third extent by multiplying the first extent by the first scaling factor, and likewise, the image processing device may adjust the second extent to produce the fourth extent by multiplying the second extent by the second scaling factor. It will be appreciated that operation 412 encompasses embodiments where the user adjusts the first extent but not the second extent, and where the user adjusts the second extent but not the first extent.

At operation 414, method 400 optionally includes the image processing device removing the streak residual from the streaky-noisy image to the third extent, and removing the noise residual from the streaky-noisy image to the fourth extent, to produce a second de-noised medical image. In some embodiments, a user may select or input a third extent, and a fourth extent, via a user input device, and in response the image processing device may produce a second weighted streak residual by multiplying the streak residual determined at operation 406 by the third extent, and may produce a second weighted noise residual by multiplying the noise residual determined at operation 406, by the fourth extent. The image processing device may subtract the second weighted streak residual and the second weighted noise residual from the streaky-noisy image to produce a second de-noised medical image. In some embodiments, if the user selects a third extent or a fourth extent less than 1.0, the second de-noised medical image may include a portion of the intensity of the streak artifacts and/or a portion of the intensity of the noise, and may therefore comprise a partially de-noised image.

At operation 416, method 400 optionally includes the image processing device displaying the second de-noised medical image. An example of a second de-noised medical image 428 is shown to the left of operation 416 in FIG. 4. Following operation 416, method 400 may end.

By producing separate outputs for the streak residual and the noise residual, an extent of streak residual removal and noise residual removal may be independently controlled, enabling different extents of removal of streak artifacts relative to noise, providing a user with greater control over an appearance of a displayed image. Further, method 400 may increase the speed of image de-noising following image acquisition, compared to conventional approaches such as CS, by distributing a portion of the computational burden, which may conventionally occur following image acquisition, to a training phase conducted prior to image acquisition. Training of a deep neural network may occupy a relatively larger portion of time and computational resources than implementation, thus, by pre-training a deep neural network to identify and extract streak residuals and noise residuals from image data, prior to image acquisition, removal of streak artifacts and noise may occur more rapidly than could be achieved by approaches such as CS, which occur de novo after image acquisition.

A technical effect of mapping a streaky-noisy image to a streak residual and a noise residual, using a trained deep neural network, is that the streak residual and noise residual may be used to separately and variably remove streak artifacts and noise, providing a user with greater control over the display appearance of acquired images. Further, by mapping the streaky-noisy image to the streak residual and the noise residual using a previously trained deep neural network, a speed of image de-noising may be increased by "pre-loading" the computational burden to a training phase occurring prior to image acquisition. Additionally, by incorporating acquisition parameters pertaining to acquisition of the streaky-noisy image, the trained deep neural network may be provided with contextual information regarding the streak artifacts and noise present in the streaky-noisy image, enabling more accurate identification and more selective removal of both the streak artifacts and the noise.

Figure 5:
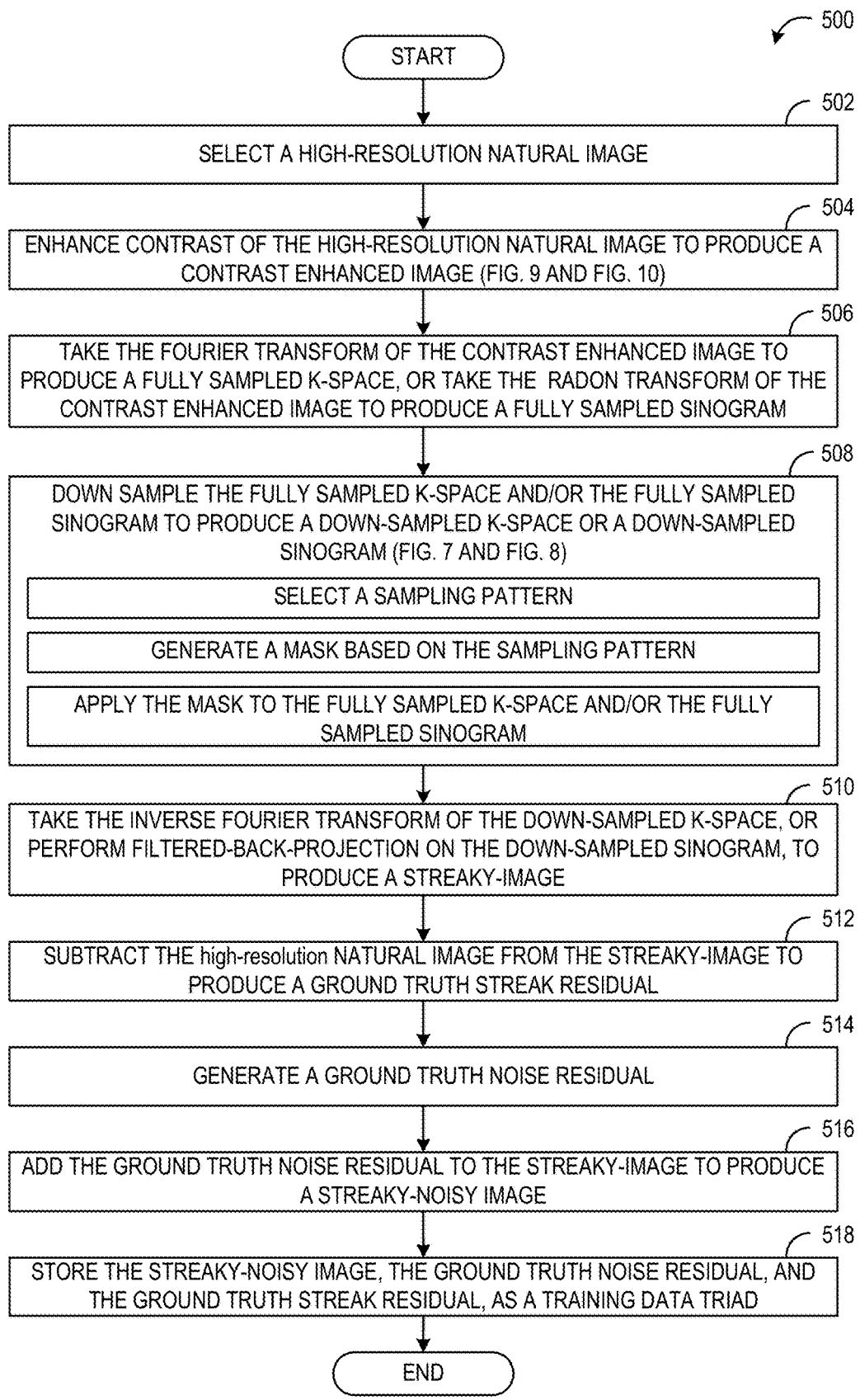
FIG. 5 is a flow chart illustrating an exemplary method for generating training data triads which may be used to train a deep neural network to infer streak residuals and noise residuals for medical images.

Turning to FIG. 5, a flowchart of an example method 500 for generating training data triads for training a deep neural network to identify and extract streak artifacts and noise from streaky-noisy images is shown. In some embodiments, a training data triad comprises three distinct elements; a ground-truth streak residual, a ground-truth noise residual, and a streaky-noisy image comprising an image overlaid with both the ground-truth streak residual and the ground-truth noise residual. The training data triads generated by method 500 may be used according to a supervised training routine, such as method 600 shown in FIG. 6, to train a deep neural network to identify and extract streak artifacts and noise present in images. Method 500 may be executed by one or more of the systems discussed above. In one embodiment, image processing device 202, executing instructions stored in training module 212, may execute one or more operations of method 500.

At operation 502, the image processing device selects a high-resolution natural image, devoid of streak artifacts and noise. Natural images may include a larger variety of images than medical images, and may include a greater information content than images generated based on a mathematical model. Further, a known limitation in the field of machine learning is the scarcity of training data, and by leveraging comparatively prevalent natural images, as opposed to a more constrained domain of images (e.g., medical images), a larger training data set may be generated. In some embodiments, at operation 502, the image processing device may access a repository of high-resolution natural images stored in non-transitory memory, and may select an image therefrom. In some embodiments, the image processing device may randomly select a high-resolution natural image using a random number generator.

At operation 504, the image processing device enhances contrast of the high-resolution natural image to produce a contrast enhanced image. In some embodiments, enhancing contrast of the high-resolution natural image selected at operation 504 comprises selecting a window-width (WW) narrower than a current WW used to display the high-resolution natural image, generating a look-up-table (LUT) comprising a mapping of pixel/voxel intensity values of the high-resolution natural image to pixel/voxel intensity values of a contrast enhanced image. The image processing device may map/transform the pixel/voxel intensity values of the high-resolution natural image using the LUT, to produce a contrast enhanced image. In other words, in some embodiments, at operation 504 the image processing device increases a lower intensity threshold, below which a pixel/voxel will be displayed as black, and decreases an upper intensity threshold, above which a pixel/voxel will be displayed as white.

Referring briefly to FIG. 9, the impact of contrast enhancement on streak artifact residual generation is illustrated by comparing a first artifact residual 906, generated using a non-contrast enhanced image 902, with artifact residual 908, generated using a contrast enhanced image 904. As can be seen, first artifact residual 906 comprises a mixture of ringing artifacts and streak artifacts, whereas second artifact residual 908 comprises primarily streak artifacts. Thus, artifact residuals generated from contrast enhanced images according to one or more operations of method 500 comprise primarily streak artifacts, enabling a deep neural network trained using artifact residuals such as second artifact residual 908 to learn to selectively identify and extract streak residuals. In other words, generation of ground-truth streak residuals from contrast enhanced images enables a deep neural network to selectively identify and extract streak artifacts, by providing the deep neural network with examples of streak artifacts, substantially devoid of other types of artifacts/noise (e.g., ringing artifacts, white-noise, blurring, colored-noise etc.).

Turning briefly to FIG. 10, a comparison between a de-noised image 1002, and a de-noised image 1004, is shown. First de-noised image 1002 was de-noised using a deep neural network trained using training data generated from non-contrast enhanced images, whereas second de-noised image 1004 was de-noised using a deep neural network trained using training data generated from contrast enhanced images. As can be see, first de-noised image 1002 comprises a substantial amount of streak artifacts, whereas as second de-noised medical image 1004 comprises significantly less streak artifacts than first de-noised image 1002.

Returning to FIG. 5, following operation 504, method 500 may proceed to operation 506. At operation 506, the image processing device may take the Fourier transform of the contrast enhanced image to produce a fully sampled k-space (an example of which is shown by fully sampled k-space 802 in FIG. 8), and/or may take the Radon transform of the contrast enhanced image to produce a fully sampled sinogram (an example of which is shown by fully sampled sinogram 702 in FIG. 7). More particularly, in embodiments where method 500 is used to generate training data for training a deep neural network to remove streak artifacts and noise from MRI images, operation 506 may include performing a 2D or 3D Fourier transform (FT) on the contrast enhanced image to produce a fully sampled 2D or 3D k-space, respectively, wherein a 2D FT is employed on 2D contrast enhanced images, and wherein a 3D FT is employed on 3D contrast enhanced images. In embodiments in which method 500 is used to generate training data for training a deep neural network to remove streak artifacts and noise from CT images, operation 506 may include performing a plurality of Radon transforms (RTs) of the contrast enhanced image to produce a fully sampled 2D or 3D sinogram.

At operation 508, the image processing device down-samples the fully sampled k-space to produce a down-sampled k-space (an example of which is shown by down-sampled k-space 804 in FIG. 8), and/or the image processing device down-samples the fully sampled sinogram to produce a down-sampled sinogram (an example of which is shown by down-sampled sinogram 704 in FIG. 7). In some embodiments, a down sampling pattern and/or a down sampling ratio may be automatically selected by the image processing device to mimic a desired undersampling pattern in a pre-determined MRI or CT imaging protocol. In some embodiments, a k-space undersampling pattern (e.g., PROPELLER, stack-of-stars, etc.) may be selected, a k-space mask may be generated based on the k-space sampling pattern (wherein the k-space mask comprises an array of 1's and 0's, corresponding to unmasked and masked regions of the fully sampled k-space, respectively), and the k-space mask may be applied to the fully sampled k-space to produce the down-sampled k-space. Similarly, in some embodiments, a sinogram undersampling pattern may be selected to mimic a sparse sinogram sampling pattern employed in a pre-determined CT imaging protocol, a sinogram mask may be generated based on sinogram sampling pattern (wherein the sinogram mask comprises an array of 1's and 0's, corresponding to unmasked and masked regions of the fully sampled sinogram, respectively), and the sinogram mask may be applied to the fully sampled sinogram to produce the down-sampled sinogram. In some embodiments, deep neural networks trained on training data generated using a particular undersampling pattern may include an indication of said undersampling pattern in metadata associated with the deep neural network. Although several examples of sampling patterns are given herein, it will be appreciated that the current disclosure encompasses substantially any sampling pattern.

At operation 510, the image processing device may take the inverse FT (IFT) of the down-sampled k-space and/or perform filtered-back-projection on the down-sampled sinogram, to produce a streaky-image (examples of which are shown by streaky-image 708, and streaky-image 808). In embodiments where the undersampled k-space comprises a 2D k-space, operation 510 comprises performing a 2D IFT on the down-sampled k-space to produce a 2D streaky-image. In embodiments where the undersampled k-space comprises a 3D k-space, operation 510 comprises performing a 3D IFT on the down-sampled k-space to produce a 3D streaky-image.

At operation 512, the image processing device subtracts the high-resolution natural image from the streaky-image to produce a ground-truth streak residual. Turning briefly to FIG. 7, an example of subtracting a high-resolution natural image 706 from a streaky-image 708 to produce a ground-truth streak residual 710, is shown. As can be seen in FIG. 7, after subtracting intensity values from each pixel/voxel of high-resolution natural image 706 from intensity values of each corresponding pixel/voxel of streaky-image 708, the intensity values remaining represent the streak artifacts induced in high-resolution natural image 706 by down sampling the fully sampled sinogram 702.

Similarly, in FIG. 8, after subtracting intensity values from each pixel/voxel of high-resolution natural image 806 from intensity values of each corresponding pixel/voxel of streaky-image 808, a ground-truth streak residual 810 may be produced, wherein the ground-truth streak residual 810 comprises the intensity values remaining (that is, the residual intensity values) represent the streak artifacts induced in high-resolution natural image 806 by down sampling the fully sampled k-space 802. FIG. 8 further illustrates a method of generating a channel combined ground-truth streak residual 816 from MR data, wherein the ground-truth streak residual 816 simulates streak artifacts which may be produced in MR images acquired using multi-channel surface coils. In MR imaging, multi-channel surface coils are often used for high SNR, large FOV and/or parallel imaging. However, unlike with large body coils, multi-channel surface coils may further increase the non-uniformity of signal, noise and/or artifacts in MR images acquired thereby. Depending on the channel combination method, MR images acquired via multi-channel surface coils may also include an uneven power distribution of noise. Channel combined high-resolution natural image 812 may be generated by applying a simulation of a channel combination algorithm to high-resolution natural image 806, and similarly, channel combined streaky-image 814 may be generated by applying the simulation of a channel combination algorithm to the streaky-image 808. A channel combined ground-truth streak residual 816 may be generated by subtracting pixel/voxel intensity values of channel combined high-resolution natural image 812 from corresponding pixel/voxel intensity values in channel combined streaky-image 814. Comparing channel combined ground-truth streak residual 816 and ground-truth streak residual 810, the distributions of streak artifacts are different because of the coil sensitivity profiles and channel combination.

At operation 514, the image processing device generates a ground-truth noise residual. In some embodiments, at operation 514 the image processing device generates white noise in an image space by randomly selecting an intensity value according to a pre-determined Gaussian distribution of intensity values, for each pixel/voxel in an array of pixels/voxels equal in size/dimension to the high-resolution natural image. In some embodiments, at operation 514 the image processing device simulates colored-noise by taking a FT of a white noise image to produce a white noise k-space, and selectively attenuates intensity of the white noise k-space according to a pre-determined pattern (e.g., by multiplying the white noise k-space by a weighting matrix), to produce a colored-noise k-space, wherein the noise intensity is not constant as a function of position in k-space. The colored-noise k-space may then be transformed into a ground-truth noise residual in image space by taking the IFT of the colored-noise k-space. In some embodiments, operation 514 includes the image processing device generating the ground-truth noise residual by generating noise having a flat spatial frequency distribution in a blank image, wherein a first size of the blank image equals a second size of the high-resolution natural image. In some embodiments, the image processing device may generate the ground-truth noise residual by generating noise having a non-flat spatial frequency distribution in a blank image, wherein a first size of the blank image matches a second size of the high-resolution natural image.

At operation 516, the image processing device performs pixel-wise/voxel-wise intensity addition for each pixel/voxel in the ground-truth noise residual and each corresponding pixel/voxel in the streaky-image, to produce a streaky-noisy image. In other words, the streaky-noisy image generated at operation 516 comprises a linear combination of intensity values from each pixel/voxel of the high-resolution natural image selected at operation 502, each pixel/voxel of the ground-truth streak residual generated at operation 512, and each pixel/voxel of the ground-truth noise residual generated at operation 514.

At operation 518, the image processing device stores the streaky-noise image, the corresponding ground-truth streak residual, and the corresponding ground-truth noise residual, as a training data triad. In some embodiments, the training data triad may be stored along with one or more pieces of metadata indicating one or more of a sampling pattern used to generated the ground-truth streak residual, a type of noise generation used to produce the ground-truth noise residual, and an indication of an extent of contrast enhancement used to generate the contrast enhanced image at operation 504. Following operation 518, method 500 may end.

Figure 6:
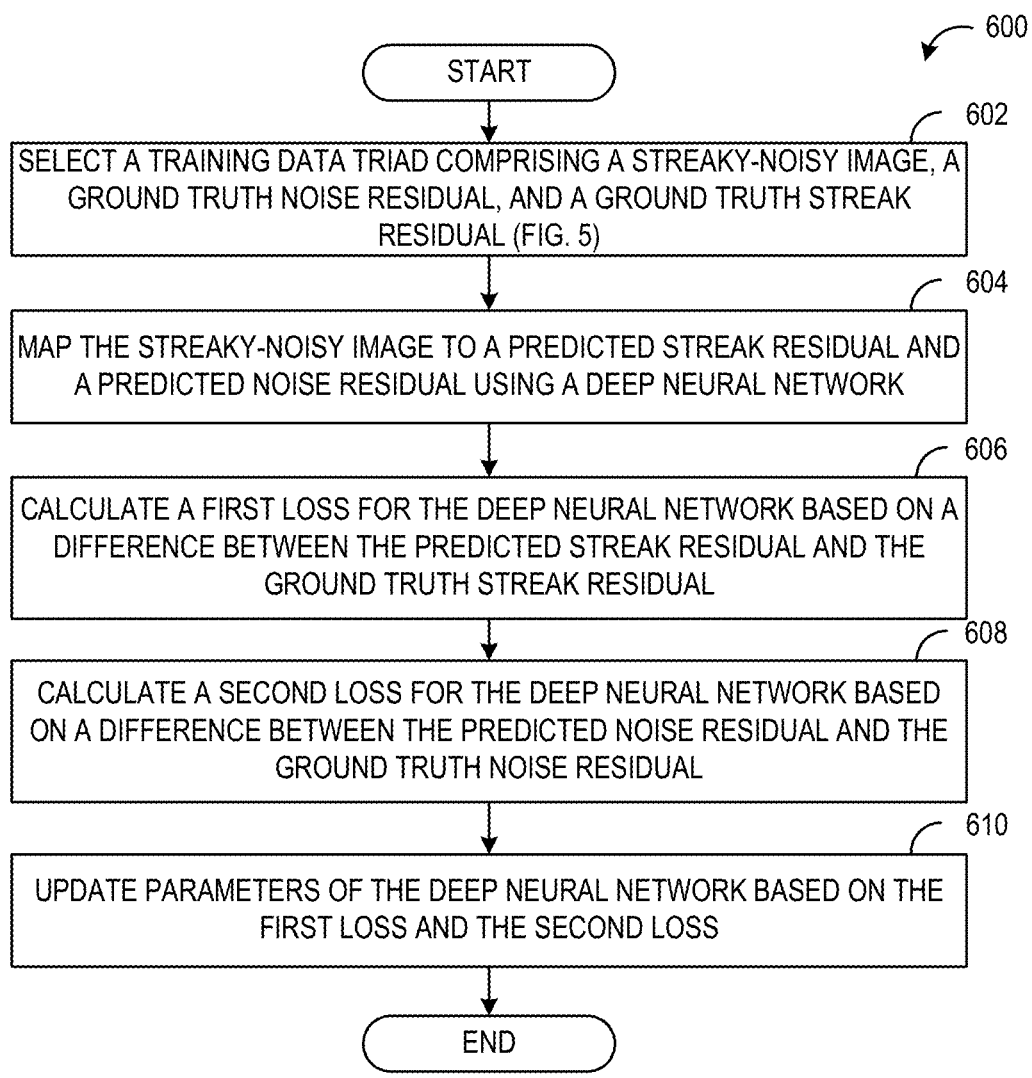
FIG. 6 is a flow chart illustrating an exemplary method for training a deep neural network to infer streak residuals and noise residuals for medical images using training data triads.

Turning to FIG. 6, a flowchart of an example method 600 for training a deep neural network (such as deep neural network 324 shown in FIG. 3) to infer a streak residual and a noise residual from an input streaky-noisy image, is shown. Method 600 may be executed by one or more of the systems discussed above. In some embodiments, method 600 may be implemented by the system 10 shown in FIG. 1 or the image processing device 202 shown in FIG. 2. In some embodiments, method 600 may be implemented by training module 212, stored in non-transitory memory 206 of image processing device 202.

At operation 602, a training data triad, from a plurality of training data triads, is fed to a deep neural network, wherein the training data triad comprises a streaky-noisy image, and a ground-truth streak residual and a ground-truth noise residual, corresponding to the streaky-noisy image. The training data triad may be intelligently selected by the image processing device based on one or more pieces of metadata associated with the training data triad. In one embodiment, method 600 may be employed to train a deep neural network to identify streak residuals in images acquired using a particular k-space or sinogram sampling pattern, and operation 602 may include the image processing device selecting a training data triad generated using said particular sampling pattern.

In some embodiments, the training data triad, and the plurality of training data triads, may be stored in an image processing device, such as in image data module 214 of image processing device 202. In other embodiments, the training data triad may be acquired via communicative coupling between the image processing device and an external storage device, such as via Internet connection to a remote server.

At operation 604, the streaky-noisy image of the training data triad is mapped to a predicted streak residual and a predicted noise residual. In some embodiments, operation 604 may comprise inputting pixel/voxel intensity data of the streaky-noisy image into an input layer of the deep neural network, identifying features present in the streaky-noisy image by propagating the image data through one or more encoding layers of the deep neural network, wherein said encoding layers may comprise one or more convolutional filters, and predicting a streak residual and a noise residual by propagating the identified features through one or more decoding layers of the deep neural network, as discussed in more detail above, with reference to FIG. 3.

At operation 606, the image processing device may calculate a first loss for the deep neural network based on a difference between the predicted streak residual determined at operation 604, and the ground-truth streak residual. Said another way, operation 606 comprises the image processing device determining an error of the predicted streak residual using the ground-truth streak residual, and a loss function. In some embodiments, operation 606 may include the image processing device determining an intensity difference between a plurality of pixels/voxels of the predicted streak residual and a plurality of pixels/voxels of the ground-truth streak residual, and inputting the plurality of intensity differences into a pre-determined loss function (e.g., a mean-squared error function, or other loss function known in the art of machine learning). In some embodiments, the first loss may comprise one or more of a Sorensen-Dice score, a mean square error, an absolute distance error, or a weighted combination of one or more of the preceding. In some embodiments, operation 606 may comprise determining a DICE score for the predicted streak residual using the ground-truth streak residual according to the following equation:

$$DICE = (S \cap T)/(S \cup T),$$

wherein S is the ground-truth streak residual, and T is the predicted streak residual. In some embodiments, both the predicted streak residual and the ground-truth streak residual comprise 3D arrays of intensity values.

At operation 608, the image processing device may calculate a second loss for the deep neural network based on a difference between the predicted noise residual determined at operation 604, and the ground-truth noise residual. Said another way, operation 608 comprises the image processing device determining an error of the predicted noise residual using the ground-truth noise residual, and a loss function. In some embodiments, operation 608 may include the image processing device determining an intensity difference between a plurality of pixels/voxels of the predicted noise residual and a plurality of pixels/voxels of the ground-truth noise residual, and inputting the plurality of intensity differences into a pre-determined loss function (e.g., a MSE function, or other loss function known in the art of machine learning). In some embodiments, the second loss may comprise one or more of a DICE score, a mean square error, an absolute distance error, or a weighted combination of one or more of the preceding. In some embodiments, operation 608 may comprise determining a DICE score for the predicted noise residual using the ground-truth noise residual according to the equation given above with reference to operation

606, wherein S is the ground-truth noise residual, and T is the predicted noise residual. In some embodiments, both the predicted noise residual and the ground-truth noise residual comprise 3D arrays of intensity values.

At operation 610, the weights and biases of the deep neural network are adjusted based on the first loss and the second loss calculated at operation 606 and at operation 608. In some embodiments, the first loss and the second loss may be alternately and separately back propagated through the layers of the deep neural network, and the parameters of the deep neural network may be updated according to a gradient descent algorithm based on the back propagated first loss and second loss. In some embodiments, the first loss and the second loss may be aggregated to produce an aggregate loss, and operation 610 may include the image processing device updating parameters of the deep neural network based on the aggregate loss. In some embodiments, an aggregate loss may be determined by the image processing device by multiplying the first loss and the second loss by a first weight and a second weight, respectively, to produce a first weighted loss and a second weighted loss, and summing the first weighted loss and the second weighted loss to produce the aggregate loss. The loss, may be back propagated through the layers of the deep neural network to update the weights (and biases) of the layers. In some embodiments, back propagation of the loss may occur according to a gradient descent algorithm, wherein a gradient of the loss function (a first derivative, or approximation of the first derivative) is determined for each weight and bias of the deep neural network. Each weight (and bias) of the deep neural network is then updated by adding the negative of the product of the gradient determined (or approximated) for the weight (or bias) and a predetermined step size, according to the below equation:

$$P_{i+1} = P_i - \text{Step} \frac{\partial(\text{loss})}{\partial P_i}$$

Where $P_{i+1}$ is the updated parameter value, $P_i$ is the previous parameter value, Step is the step size, and $$\frac{\partial(\text{loss})}{\partial P_i}$$

is the partial derivative of the loss with respect to the previous parameter.

Following operation 608, method 600 may end. It will be noted that method 600 may be repeated until the weights and biases of the deep neural network converge, a threshold difference metric is obtained (for the training data or on a separate validation dataset), or the rate of change of the weights and/or biases of the deep neural network for each iteration of method 600 are under a threshold. In this way, method 600 enables a deep neural network to be trained to infer streak residuals and noise residuals present in streaky-noisy images.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method for training a deep neural network comprising:
   generating a training data triad, wherein the training data triad comprises;
      an image including streak artifacts and noise;
      a ground-truth streak residual; and
      a ground-truth noise residual;
   mapping the image to a predicted streak residual and a predicted noise residual using a deep neural network;
   calculating a first loss for the deep neural network based on a difference between the predicted streak residual and the ground-truth streak residual;
   calculating a second loss for the deep neural network based on a difference between the predicted noise residual and the ground-truth noise residual; and
   updating parameters of the deep neural network based on the first loss and the second loss.

2. The method of claim 1, wherein generating the training data triad comprises:
   selecting a high-resolution natural image;
   enhancing contrast of the high-resolution natural image to produce a contrast enhanced image;
   taking a Fourier transform (FT) of the contrast enhanced image to produce a fully sampled k-space;
   down-sampling the fully sampled k-space to produce a down-sampled k-space;
   taking an inverse FT of the down-sampled k-space to produce a streaky-image;
   subtracting the high-resolution natural image from the streaky-image to produce the ground-truth streak residual;
   generating the ground-truth noise residual;
   adding the ground-truth noise residual to the streaky-image to produce the image including streak artifacts and noise;
   storing the image, the ground-truth streak residual, and the ground-truth noise residual, as the training data triad.

3. The method of claim 2, wherein generating the ground-truth noise residual comprises:

generating noise having a flat spatial frequency distribution in a blank image, wherein a first size of the blank image equals a second size of the high-resolution natural image.

4. The method of claim 2, wherein generating the ground-truth noise residual comprises:
generating noise having a non-flat spatial frequency distribution in a blank image, wherein a first size of the blank image matches a second size of the high-resolution natural image.

5. The method of claim 2, wherein down-sampling the fully sampled k-space to produce a down-sampled k-space comprises:
selecting a sampling pattern;
generating a k-space mask based on the sampling pattern;
applying the k-space mask to the fully sampled k-space to produce the down-sampled k-space.

6. The method of claim 5, wherein the sampling pattern comprises a radial under-sampling of the fully sampled k-space.

7. The method of claim 1, wherein generating the training data triad comprises:
selecting a high-resolution natural image;
enhancing contrast of the high-resolution natural image to produce a contrast enhanced image;
taking a Radon transform (RT) of the contrast enhanced image to produce a sinogram;
down-sampling the sinogram to produce a down-sampled sinogram;
performing filtered-back-projection (FBP) on the down-sampled sinogram to produce a streaky-image;
subtracting the high-resolution natural image from the streaky-image to produce the ground-truth streak residual;
generating the ground-truth noise residual;
adding the ground-truth noise residual to the streaky-image to produce the image including streak artifacts and noise;
storing the image, the ground-truth streak residual, and the ground-truth noise residual, as the training data triad.

8. The method of claim 7, wherein down-sampling the sinogram to produce the down-sampled sinogram comprises:
selecting a sampling pattern;
generating a sinogram mask based on the sampling pattern;
applying the sinogram mask to the sinogram to produce the down-sampled sinogram.

* * * * *